US010010482B2

(12) United States Patent
Davidian et al.

(10) Patent No.: US 10,010,482 B2
(45) Date of Patent: Jul. 3, 2018

(54) SYRINGE FILL SYSTEM AND METHOD

(71) Applicant: ANUTRA MEDICAL, INC., Morrisville, NC (US)

(72) Inventors: Daniel K. Davidian, Raleigh, NC (US); Scott G. Newnam, Morrisville, NC (US); Eli B. Nichols, Durham, NC (US); Theodore J. Mosler, Raleigh, NC (US)

(73) Assignee: ANUTRA MEDICAL, INC., Morrisville, NC (US)

( * ) Notice: Subject to any disclaimer, the term of this patent is extended or adjusted under 35 U.S.C. 154(b) by 10 days.

(21) Appl. No.: 15/208,568

(22) Filed: Jul. 12, 2016

(65) Prior Publication Data

US 2016/0317390 A1    Nov. 3, 2016

Related U.S. Application Data

(63) Continuation of application No. 14/298,716, filed on Jun. 6, 2014, now Pat. No. 9,387,151.
(Continued)

(51) Int. Cl.
*A61J 1/20* (2006.01)
*A61M 5/178* (2006.01)
(Continued)

(52) U.S. Cl.
CPC ............. *A61J 1/2096* (2013.01); *A61J 1/201* (2015.05); *A61J 1/2075* (2015.05); *A61J 1/22* (2013.01);
(Continued)

(58) Field of Classification Search
CPC ............. A61M 5/502; A61M 5/31593; A61M 5/31591; A61M 5/31586; A61M 5/3137;
(Continued)

(56) References Cited

U.S. PATENT DOCUMENTS 2,373,520 A    4/1945  Wallin
2,409,656 A    10/1946 Austin
(Continued)

FOREIGN PATENT DOCUMENTS

AU    2011101361 A4    12/2011
EP    0115931 A1    8/1984
(Continued)

OTHER PUBLICATIONS

University of California, San Francisco, "Comparison of Pain of Conventional to Buffered Local Anesthesia During Injection in Pediatric Dental Patients (BufferDent)", "ClinicalTrials.gov Identifier No. NCT01622296, Accessed via http://clinicaltrials.gov/ct2/show/NCT01622296", Feb. 10, 2014, Page(s) (Abstract).
(Continued)

*Primary Examiner* — Timothy L Maust
*Assistant Examiner* — Andrew Schmid
(74) *Attorney, Agent, or Firm* — Hultquist, PLLC; Steven J. Hultquist

(57) ABSTRACT

A syringe fill system is described, which is useful for filling syringes for dental anesthetic applications. The system incorporates capability for "push-pull", "pull-push", "push-push", and "pull-pull" modes of operation, for loading syringes with compositions comprising multiple fluid components. A syringe fillable by such syringe fill systems is described, providing haptic and audible feedback to a user, to aid in administering precise amounts of therapeutic compositions. Also disclosed are cassette assemblies for use in such syringe fill systems. Such cassette assemblies may be formed of plastic and elastomeric materials of construction, as disposable or single-use components of the syringe fill system.

20 Claims, 23 Drawing Sheets

Related U.S. Application Data

(60) Provisional application No. 61/867,645, filed on Aug. 20, 2013, provisional application No. 61/923,918, filed on Jan. 6, 2014.

(51) Int. Cl.
| | | |
|---|---|---|
| *A61M 5/315* | (2006.01) | |
| *A61J 1/22* | (2006.01) | |
| *A61M 5/00* | (2006.01) | |
| *A61M 5/31* | (2006.01) | |
| *A61M 5/24* | (2006.01) | |
| *A61M 5/50* | (2006.01) | |

(52) U.S. Cl.
CPC ...... *A61M 5/1782* (2013.01); *A61M 5/31586* (2013.01); *A61M 5/31591* (2013.01); *A61M 5/31593* (2013.01); *A61J 1/2055* (2015.05); *A61M 5/001* (2013.01); *A61M 5/2425* (2013.01); *A61M 5/2448* (2013.01); *A61M 5/3137* (2013.01); *A61M 5/502* (2013.01); *A61M 2202/048* (2013.01); *A61M 2205/75* (2013.01)

(58) Field of Classification Search
CPC .............. A61M 5/2448; A61M 5/2425; A61M 5/1782; A61M 5/001; A61M 2205/75; A61J 2001/2082; A61J 1/22; A61J 1/2096; A61J 1/2075; A61J 1/2055; A61J 1/201
USPC ... 141/302, 301, 290, 27, 25, 238, 236, 235, 141/234, 2, 18, 107, 105, 104, 100
See application file for complete search history.

(56) References Cited

U.S. PATENT DOCUMENTS

| | | | |
|---|---|---|---|
| 2,474,496 A | 6/1947 | Rayman | |
| 2,502,639 A | 4/1950 | Blake | |
| 2,695,023 A | 11/1954 | Brown | |
| 2,707,954 A | 5/1955 | Kas | |
| 2,764,981 A | 10/1956 | Helmer et al. | |
| 3,747,812 A | 7/1973 | Karman et al. | |
| 3,844,318 A | 10/1974 | Raia et al. | |
| 4,246,898 A | 1/1981 | Travalent et al. | |
| 4,378,428 A | 3/1983 | Farina et al. | |
| 4,432,758 A | 2/1984 | Finegold | |
| 4,439,184 A | 3/1984 | Wheeler | |
| 4,466,426 A | 8/1984 | Blackman | |
| 4,469,482 A | 9/1984 | Lissenburg et al. | |
| 4,501,306 A | 2/1985 | Chu et al. | |
| 4,613,328 A | 9/1986 | Boyd | |
| 4,617,016 A | 10/1986 | Blomberg | |
| 4,642,102 A | 2/1987 | Ohmori | |
| 4,654,035 A | 3/1987 | Ando | |
| 4,664,655 A | 5/1987 | Orentreich et al. | |
| 4,722,733 A | 2/1988 | Howson | |
| 4,747,824 A | 5/1988 | Spinello | |
| 4,787,893 A * | 11/1988 | Villette .................. | A61C 19/08 433/118 |
| 4,822,339 A | 4/1989 | Tran | |
| 4,883,101 A * | 11/1989 | Strong ................ | A61M 5/1782 141/27 |
| 4,929,238 A | 5/1990 | Baum | |
| 4,950,163 A | 8/1990 | Zimble | |
| 4,998,570 A | 3/1991 | Strong | |
| 5,007,904 A | 4/1991 | Densmore et al. | |
| D320,276 S | 9/1991 | Baum | |
| D321,053 S | 10/1991 | Baum | |
| RE33,821 E | 2/1992 | Banks | |
| 5,131,403 A | 7/1992 | Haynes | |
| 5,147,323 A | 9/1992 | Haber et al. | |
| 5,149,320 A | 9/1992 | Dhaliwal et al. | |
| 5,176,646 A * | 1/1993 | Kuroda ............... | A61M 5/1456 128/DIG. 1 |
| 5,209,724 A | 5/1993 | Dhaliwal et al. | |
| 5,226,901 A | 7/1993 | Dhaliwal et al. | |
| 5,261,903 A | 11/1993 | Dhaliwal et al. | |
| 5,269,762 A * | 12/1993 | Armbruster ........... | A61M 5/20 604/131 |
| 5,272,139 A | 12/1993 | Cary, Jr. | |
| 5,298,023 A | 3/1994 | Haber et al. | |
| 5,304,165 A | 4/1994 | Haber et al. | |
| 5,328,476 A | 7/1994 | Bidwell | |
| 5,329,976 A * | 7/1994 | Haber .................. | A61J 1/2089 141/18 |
| 5,378,233 A | 1/1995 | Haber et al. | |
| 5,380,295 A | 1/1995 | Vacca | |
| 5,391,157 A | 2/1995 | Harris et al. | |
| 5,405,362 A | 4/1995 | Kramer et al. | |
| 5,405,376 A | 4/1995 | Mulier et al. | |
| 5,456,670 A | 10/1995 | Neer et al. | |
| 5,518,730 A | 5/1996 | Fuisz | |
| 5,534,620 A | 7/1996 | Oh et al. | |
| 5,563,153 A | 10/1996 | Mueller et al. | |
| 5,585,243 A | 12/1996 | Aster et al. | |
| 5,603,695 A | 2/1997 | Erickson | |
| 5,647,851 A * | 7/1997 | Pokras .................... | A61M 5/20 604/131 |
| 5,672,155 A * | 9/1997 | Riley ...................... | A61M 5/20 604/131 |
| 5,690,618 A | 11/1997 | Smith et al. | |
| 5,900,416 A | 5/1999 | Markson | |
| 5,911,252 A | 6/1999 | Cassel | |
| 5,927,349 A | 7/1999 | Martucci et al. | |
| 6,035,904 A | 3/2000 | Beau et al. | |
| 6,133,040 A | 10/2000 | Glattstein | |
| 6,202,708 B1 | 3/2001 | Bynum | |
| 6,258,374 B1 | 7/2001 | Freiss et al. | |
| 6,379,373 B1 | 4/2002 | Sawhney et al. | |
| D461,891 S | 8/2002 | Moberg | |
| 6,478,779 B1 | 11/2002 | Hu | |
| 6,526,980 B1 | 3/2003 | Tracy et al. | |
| 6,560,975 B1 | 5/2003 | Weldon et al. | |
| 6,579,269 B1 | 6/2003 | Kleyman | |
| 6,626,863 B1 | 9/2003 | Berler et al. | |
| 6,627,620 B1 | 9/2003 | Nielsen | |
| 6,723,068 B2 | 4/2004 | Lavi et al. | |
| 6,764,678 B2 | 7/2004 | Weber et al. | |
| 6,905,688 B2 | 6/2005 | Rosen et al. | |
| 6,913,761 B1 | 7/2005 | Trigg et al. | |
| 6,924,273 B2 | 8/2005 | Pierce | |
| 6,946,134 B1 | 9/2005 | Rosen et al. | |
| 6,972,006 B2 | 12/2005 | Ferguson | |
| 6,994,857 B2 | 2/2006 | Rosen et al. | |
| 7,044,125 B2 | 5/2006 | Vedrine et al. | |
| 7,153,285 B2 | 12/2006 | Lauman et al. | |
| 7,174,923 B2 | 2/2007 | Schorn et al. | |
| 7,229,630 B2 | 6/2007 | Chen et al. | |
| D547,859 S | 7/2007 | Choi | |
| 7,261,889 B2 | 8/2007 | Weber et al. | |
| 7,287,983 B2 | 10/2007 | Ilan | |
| 7,476,216 B2 | 1/2009 | Takatsuka et al. | |
| 7,482,013 B2 | 1/2009 | Ballance et al. | |
| 7,507,413 B2 | 3/2009 | Rosen et al. | |
| 7,569,230 B2 | 8/2009 | Chen et al. | |
| 7,575,757 B2 | 8/2009 | Chen et al. | |
| 7,597,687 B2 | 10/2009 | Pauza et al. | |
| 7,608,258 B2 | 10/2009 | Mishra et al. | |
| 7,611,495 B1 | 11/2009 | Gianturco | |
| 7,612,181 B2 | 11/2009 | Wu et al. | |
| D614,497 S | 4/2010 | Pola | |
| 7,700,739 B2 | 4/2010 | Lacy et al. | |
| 7,704,231 B2 | 4/2010 | Pongpairochana et al. | |
| 7,708,717 B2 | 5/2010 | Estes et al. | |
| 7,767,429 B2 | 8/2010 | Bookbinder et al. | |
| 7,785,599 B2 | 8/2010 | Ballance et al. | |
| 7,794,410 B2 | 9/2010 | Mikulka et al. | |
| 7,799,760 B2 | 9/2010 | Berlanga Acosta et al. | |
| 7,803,392 B2 | 9/2010 | Mumper et al. | |
| 7,809,254 B2 | 10/2010 | Lindsay et al. | |
| 7,829,086 B2 | 11/2010 | Hilbert et al. | |

(56) References Cited

U.S. PATENT DOCUMENTS

| | | |
|---|---|---|
| 7,863,426 B2 | 1/2011 | Wan et al. |
| 7,883,487 B2 | 2/2011 | Shantha et al. |
| 7,883,488 B2 | 2/2011 | Shantha et al. |
| 7,901,384 B2 | 3/2011 | Kleyman et al. |
| 7,915,388 B2 | 3/2011 | Wu et al. |
| D640,368 S | 6/2011 | Fujioka et al. |
| 7,968,684 B2 | 6/2011 | Ghayur et al. |
| 8,002,745 B2 | 8/2011 | Kaal et al. |
| 8,044,175 B2 | 10/2011 | Dransfield et al. |
| 8,075,547 B2 | 12/2011 | Lee |
| 8,105,294 B2 | 1/2012 | Araki et al. |
| 8,124,120 B2 | 2/2012 | Sadozai et al. |
| 8,162,917 B2 | 4/2012 | Stepovich et al. |
| 8,192,420 B2 | 6/2012 | Morriss et al. |
| 8,226,631 B2 | 7/2012 | Boyd et al. |
| 8,231,876 B2 | 7/2012 | Wan et al. |
| 8,258,268 B2 | 9/2012 | Wu et al. |
| 8,276,589 B2 | 10/2012 | Hartnick et al. |
| 8,283,162 B2 | 10/2012 | Yoshimura et al. |
| 8,287,940 B2 | 10/2012 | Von Holst et al. |
| 8,288,343 B2 | 10/2012 | Horiba et al. |
| 8,288,347 B2 | 10/2012 | Collette et al. |
| 8,303,566 B2 | 11/2012 | Stepovich et al. |
| 8,323,651 B2 | 12/2012 | Gu et al. |
| 8,323,653 B2 | 12/2012 | Damschroder et al. |
| 8,338,375 B2 | 12/2012 | Schroeder et al. |
| 8,361,051 B2 | 1/2013 | Ezeude |
| 8,631,789 B2 | 1/2014 | Virr et al. |
| 8,777,040 B2 | 7/2014 | Wahl |
| 8,905,985 B2 | 12/2014 | Allen et al. |
| 8,911,404 B2 | 12/2014 | Kim |
| 8,939,959 B2 | 1/2015 | Baney et al. |
| 9,044,549 B2 | 6/2015 | Niklasson |
| D750,768 S | 3/2016 | Davidian et al. |
| 9,387,151 B2 | 7/2016 | Davidian et al. |
| 9,393,177 B2 | 7/2016 | Davidian et al. |
| D763,433 S | 8/2016 | Davidian et al. |
| 2001/0051595 A1 | 12/2001 | Lyons et al. |
| 2002/0004643 A1 | 1/2002 | Carmel et al. |
| 2002/0006435 A1 | 1/2002 | Samuels et al. |
| 2002/0010428 A1* | 1/2002 | Vedrine ............... A61M 11/06 604/187 |
| 2002/0039594 A1 | 4/2002 | Unger |
| 2002/0107188 A1 | 8/2002 | Dunn |
| 2002/0182600 A1 | 12/2002 | Smith |
| 2002/0188327 A1 | 12/2002 | Struble |
| 2003/0055386 A1 | 3/2003 | Strauss et al. |
| 2003/0060415 A1 | 3/2003 | Hung |
| 2003/0087878 A1 | 5/2003 | Vinten-Johansen et al. |
| 2003/0093157 A1 | 5/2003 | Casares et al. |
| 2003/0133986 A1 | 7/2003 | Tsao |
| 2003/0163090 A1 | 8/2003 | Blomquist et al. |
| 2003/0181426 A1 | 9/2003 | Eisenach |
| 2003/0192791 A1 | 10/2003 | Eek |
| 2004/0025866 A1 | 2/2004 | Vedrine et al. |
| 2004/0072809 A1 | 4/2004 | Demopolos et al. |
| 2004/0131665 A1 | 7/2004 | Wepfer |
| 2004/0142968 A1 | 7/2004 | Price et al. |
| 2004/0209228 A1 | 10/2004 | Ilan |
| 2004/0241245 A1 | 12/2004 | Lu et al. |
| 2004/0247628 A1 | 12/2004 | Lintz et al. |
| 2004/0249016 A1 | 12/2004 | Allred |
| 2005/0080043 A1 | 4/2005 | Shahinian, Jr. |
| 2005/0107294 A1 | 5/2005 | Acosta et al. |
| 2005/0136122 A1 | 6/2005 | Sadozai et al. |
| 2005/0165097 A1 | 7/2005 | Weber et al. |
| 2005/0197618 A1 | 9/2005 | Plummer et al. |
| 2005/0197650 A1 | 9/2005 | Sugimoto et al. |
| 2005/0214376 A1 | 9/2005 | Faure et al. |
| 2005/0238733 A1 | 10/2005 | Henry |
| 2005/0287134 A1 | 12/2005 | Klein |
| 2005/0287199 A1 | 12/2005 | Denney et al. |
| 2006/0013834 A1 | 1/2006 | Clemente et al. |
| 2006/0013862 A1 | 1/2006 | Held |
| 2006/0034825 A1 | 2/2006 | Charron |
| 2006/0051406 A1 | 3/2006 | Parmar et al. |
| 2006/0073189 A1 | 4/2006 | Pinney et al. |
| 2006/0079558 A1 | 4/2006 | Aberg et al. |
| 2006/0079559 A1 | 4/2006 | Aberg et al. |
| 2006/0095016 A1 | 5/2006 | Pauza et al. |
| 2006/0147498 A1 | 7/2006 | Jonsson et al. |
| 2006/0169348 A1 | 8/2006 | Yigal |
| 2006/0198891 A1 | 9/2006 | Ravenelle et al. |
| 2006/0257488 A1 | 11/2006 | Hubbard |
| 2006/0264897 A1 | 11/2006 | Lobl et al. |
| 2007/0003584 A1 | 1/2007 | Anderson |
| 2007/0020194 A1 | 1/2007 | Greenway, III et al. |
| 2007/0020195 A1 | 1/2007 | Greenway, III et al. |
| 2007/0020298 A1 | 1/2007 | Pipkin et al. |
| 2007/0020299 A1 | 1/2007 | Pipkin et al. |
| 2007/0027426 A1 | 2/2007 | Matsumura et al. |
| 2007/0077544 A1 | 4/2007 | Lemperle et al. |
| 2007/0078435 A1 | 4/2007 | Stone et al. |
| 2007/0092858 A1 | 4/2007 | Usmani et al. |
| 2007/0102010 A1 | 5/2007 | Lemperle et al. |
| 2007/0104791 A1 | 5/2007 | Popov et al. |
| 2007/0151984 A1 | 7/2007 | Baker et al. |
| 2007/0172508 A1 | 7/2007 | Zupkas et al. |
| 2007/0173736 A1 | 7/2007 | Feuer et al. |
| 2007/0196914 A1 | 8/2007 | Murray et al. |
| 2007/0233001 A1* | 10/2007 | Burroughs ............ A61M 5/008 604/131 |
| 2007/0286881 A1 | 12/2007 | Burkinshsw |
| 2008/0020044 A1 | 1/2008 | Alam et al. |
| 2008/0021068 A1 | 1/2008 | Alam et al. |
| 2008/0021411 A1 | 1/2008 | Weinberg et al. |
| 2008/0058719 A1 | 3/2008 | Edwards et al. |
| 2008/0103564 A1 | 5/2008 | Burkinshaw et al. |
| 2008/0255521 A1 | 10/2008 | Kubo et al. |
| 2008/0287866 A1 | 11/2008 | Heller |
| 2008/0293637 A1 | 11/2008 | Schroeder et al. |
| 2008/0312139 A1 | 12/2008 | Acosta et al. |
| 2009/0004281 A1 | 1/2009 | Nghiem et al. |
| 2009/0029366 A1 | 1/2009 | Vasylyev et al. |
| 2009/0042968 A1 | 2/2009 | Whiting et al. |
| 2009/0053290 A1 | 2/2009 | Sand et al. |
| 2009/0054837 A1 | 2/2009 | Von Holst et al. |
| 2009/0093755 A1 | 4/2009 | Schroeder et al. |
| 2009/0093792 A1 | 4/2009 | Gross et al. |
| 2009/0101474 A1 | 4/2009 | Yuyama |
| 2009/0123527 A1 | 5/2009 | Alam et al. |
| 2009/0130017 A1 | 5/2009 | Allen et al. |
| 2009/0143436 A1 | 6/2009 | Weg |
| 2009/0159086 A1 | 6/2009 | Hartnick et al. |
| 2009/0163848 A1 | 6/2009 | Morriss et al. |
| 2009/0169607 A1 | 7/2009 | Keller et al. |
| 2009/0198145 A1 | 8/2009 | Chow |
| 2009/0198208 A1* | 8/2009 | Stavsky ............... A61J 1/2096 604/407 |
| 2009/0221984 A1 | 9/2009 | Girgis et al. |
| 2009/0234322 A1 | 9/2009 | Fischer |
| 2009/0291129 A1 | 11/2009 | Parmar et al. |
| 2009/0311311 A1 | 12/2009 | Shantha et al. |
| 2009/0312706 A1 | 12/2009 | Shantha et al. |
| 2009/0324678 A1 | 12/2009 | Thorne et al. |
| 2009/0325163 A1 | 12/2009 | Helgadottir et al. |
| 2010/0003237 A1 | 1/2010 | Keller et al. |
| 2010/0028406 A1 | 2/2010 | Kalia et al. |
| 2010/0030188 A1 | 2/2010 | Xia |
| 2010/0042137 A1 | 2/2010 | Oronsky et al. |
| 2010/0082009 A1 | 4/2010 | Wittig et al. |
| 2010/0099624 A1 | 4/2010 | Schroeder et al. |
| 2010/0136062 A1 | 6/2010 | Fernandez Montequin et al. |
| 2010/0137816 A1 | 6/2010 | Pauza et al. |
| 2010/0143327 A1 | 6/2010 | Pauza et al. |
| 2010/0178269 A1 | 7/2010 | Markham |
| 2010/0183723 A1 | 7/2010 | Laurent-Applegate et al. |
| 2010/0190735 A1 | 7/2010 | Bhasin |
| 2010/0196471 A1 | 8/2010 | Jain et al. |
| 2010/0211005 A1 | 8/2010 | Edwards et al. |
| 2010/0221756 A1 | 9/2010 | Sainte-Laudy et al. |
| 2010/0247668 A1 | 9/2010 | Eliasof et al. |
| 2010/0291056 A1 | 11/2010 | Mosher et al. |
| 2010/0303873 A1 | 12/2010 | Piron et al. |

(56) References Cited

U.S. PATENT DOCUMENTS

| | | |
|---|---|---|
| 2010/0311705 A1 | 12/2010 | Demopulos et al. |
| 2010/0318040 A1 | 12/2010 | Kelley, III et al. |
| 2010/0331770 A1 | 12/2010 | Lee et al. |
| 2011/0002896 A1 | 1/2011 | Kolodney et al. |
| 2011/0004143 A1 | 1/2011 | Beiriger et al. |
| 2011/0005958 A1 | 1/2011 | Stepovich et al. |
| 2011/0008436 A1 | 1/2011 | Altman et al. |
| 2011/0033503 A1 | 2/2011 | Sinko et al. |
| 2011/0059117 A1 | 3/2011 | Seigfried |
| 2011/0062703 A1* | 3/2011 | Lopez .................. A61J 1/2096 285/129.1 |
| 2011/0094619 A1 | 4/2011 | Steel et al. |
| 2011/0118701 A1 | 5/2011 | Baney et al. |
| 2011/0165017 A1 | 7/2011 | Christian et al. |
| 2011/0238009 A1 | 9/2011 | Meron et al. |
| 2011/0238021 A1 | 9/2011 | Hillhouse |
| 2011/0247722 A1 | 10/2011 | Stepovich et al. |
| 2011/0275979 A1 | 11/2011 | D'Ambola et al. |
| 2011/0282316 A1 | 11/2011 | Stepovich et al. |
| 2011/0284012 A1 | 11/2011 | McCollough |
| 2011/0318405 A1 | 12/2011 | Erwin |
| 2011/0319975 A1 | 12/2011 | Ho et al. |
| 2012/0029085 A1 | 2/2012 | MacKay et al. |
| 2012/0034307 A1 | 2/2012 | Alam et al. |
| 2012/0089088 A1 | 4/2012 | Foshee et al. |
| 2012/0109106 A1 | 5/2012 | Klein |
| 2012/0180432 A1 | 7/2012 | Stepovich et al. |
| 2012/0190644 A1 | 7/2012 | D'este et al. |
| 2012/0196830 A1 | 8/2012 | Parsons |
| 2012/0197184 A1 | 8/2012 | Okuda et al. |
| 2012/0214874 A1 | 8/2012 | Buyuktimkin et al. |
| 2012/0220923 A1 | 8/2012 | Morriss et al. |
| 2012/0279179 A1 | 11/2012 | Stepovich et al. |
| 2012/0291909 A1 | 11/2012 | Stepovich et al. |
| 2012/0302986 A1 | 11/2012 | Brem et al. |
| 2012/0310203 A1 | 12/2012 | Khaled et al. |
| 2012/0322767 A1 | 12/2012 | Bruzzese |
| 2012/0330228 A1 | 12/2012 | Day et al. |
| 2013/0046270 A1 | 2/2013 | Foshee et al. |
| 2013/0085465 A1 | 4/2013 | Stepovich et al. |
| 2013/0110039 A1 | 5/2013 | Just |
| 2013/0184682 A1 | 7/2013 | Austin et al. |
| 2013/0197446 A1 | 8/2013 | Gustafsson et al. |
| 2013/0220484 A1 | 8/2013 | De Marco |
| 2013/0245565 A1 | 9/2013 | Leak et al. |
| 2013/0261556 A1 | 10/2013 | Jones et al. |
| 2013/0265846 A1 | 10/2013 | Bublewitz et al. |
| 2013/0267908 A1 | 10/2013 | Leak et al. |
| 2013/0269825 A1 | 10/2013 | Osborn et al. |
| 2014/0364831 A1 | 12/2014 | Ciancarelli |
| 2014/0373968 A1 | 12/2014 | Mueller |
| 2015/0020920 A1 | 1/2015 | Lev et al. |
| 2015/0053306 A1 | 2/2015 | Davidian et al. |
| 2015/0057638 A1 | 2/2015 | Davidian et al. |
| 2015/0151041 A1 | 6/2015 | Yodfat et al. |
| 2015/0260726 A1 | 9/2015 | Refvik |
| 2015/0283321 A1 | 10/2015 | Dang et al. |
| 2015/0374916 A1 | 12/2015 | Bertolote et al. |
| 2016/0030671 A1 | 2/2016 | Tennican et al. |

FOREIGN PATENT DOCUMENTS

| | | |
|---|---|---|
| EP | 2446912 A1 | 5/2012 |
| WO | 2005072797 A1 | 8/2005 |
| WO | 2011139921 A2 | 11/2011 |
| WO | 2015026423 A1 | 2/2015 |

OTHER PUBLICATIONS

Onpharma, Inc., "Onpharma Cartridge Connector", "Accessed via http://www.onpharma.com/CartridgeConnector.html", Sep. 15, 2014, pp. 1-2.

Onpharma, Inc., "Onpharma Mixing Pen", "Accessed via http://www.onpharma.com/MixingPen.html", Sep. 15, 2014, pp. 1-2.

Onpharma, Inc., "Onset Sodium Bicarbonate Inj., 8.4 percent, USP Neutralizing Additive Solution", "Accessed via http://www.onpharma.com/SodiumBicarbonate.html", Sep. 15, 2014, pp. 1-2.

patientsville.com, "50 ML Sodium Bicarbonate 7.5% Prefilled Syringe dose and 50 ML Sodium Bicarbonate 7.5% Prefilled Syringe uses", "Accessed via http://patientsville.com/labels/50-ML-sodium-bicarbonate-7.5-%25-Prefilled-Syringe_label.htm", Jan. 2007, pp. 1-8.

Yukon Medical, "Vialok Vented Vial Access, Copyright 2013", "Accessed vial http://yukonmedical.com/products/vialok-vented-vial-access on May 20, 2014", p. 1.

Co-pending Unpublished Design U.S. Appl. No. 29/493,299, filed Jun. 6, 2014.

\* cited by examiner

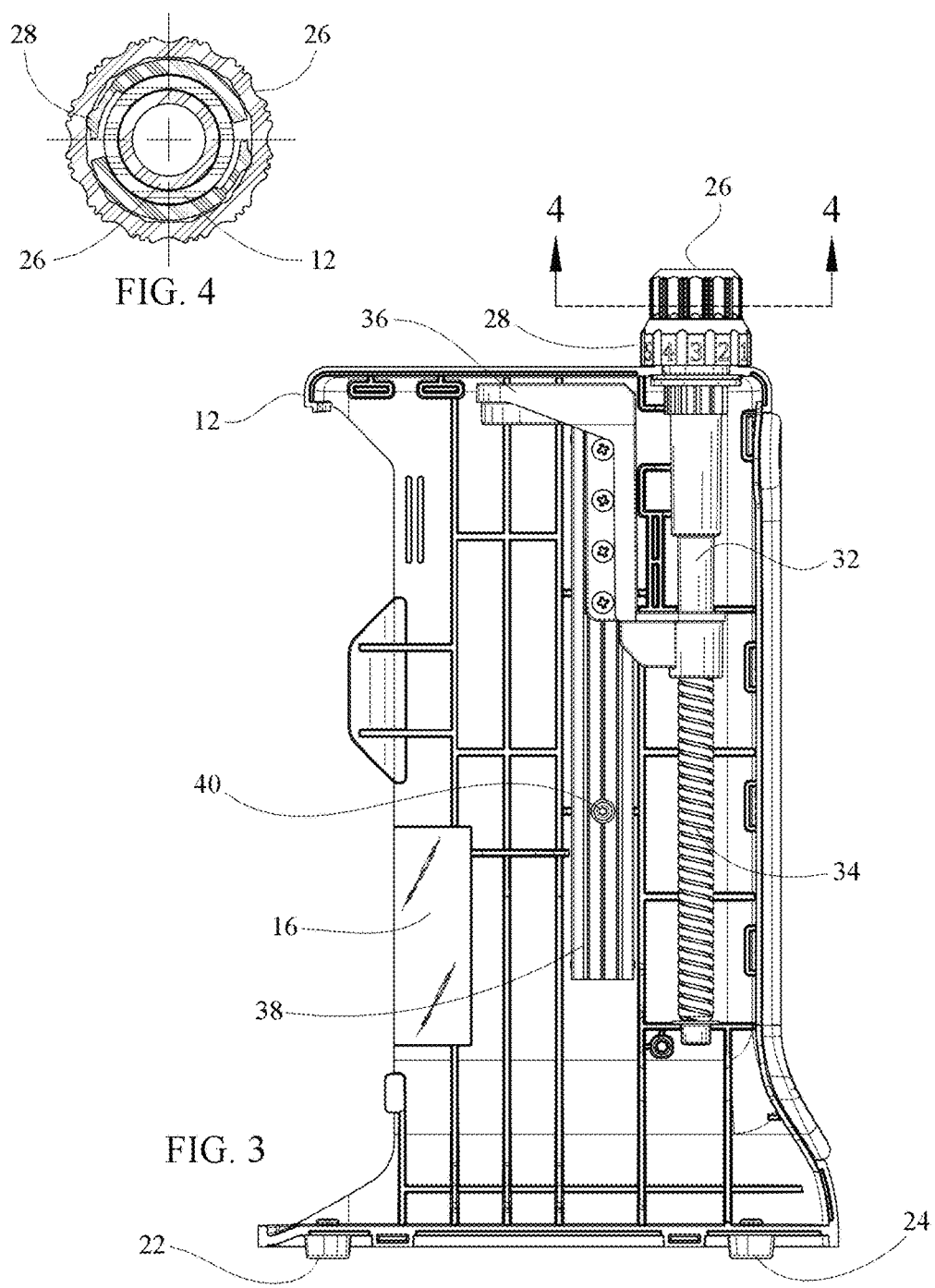

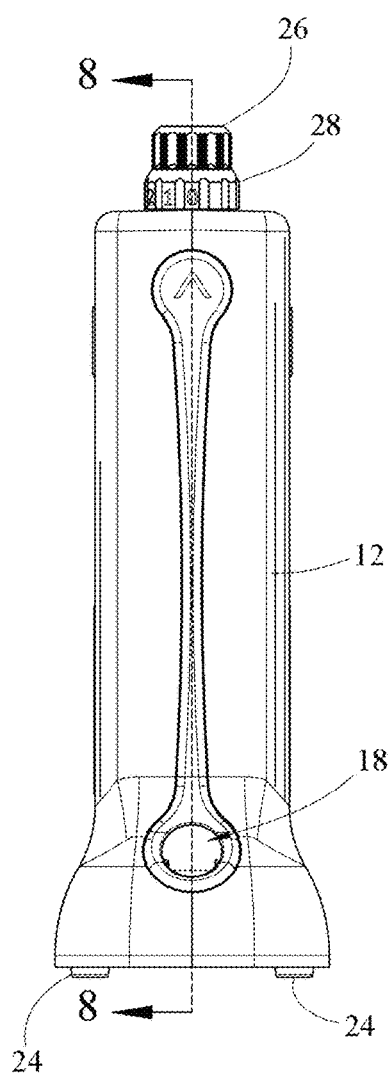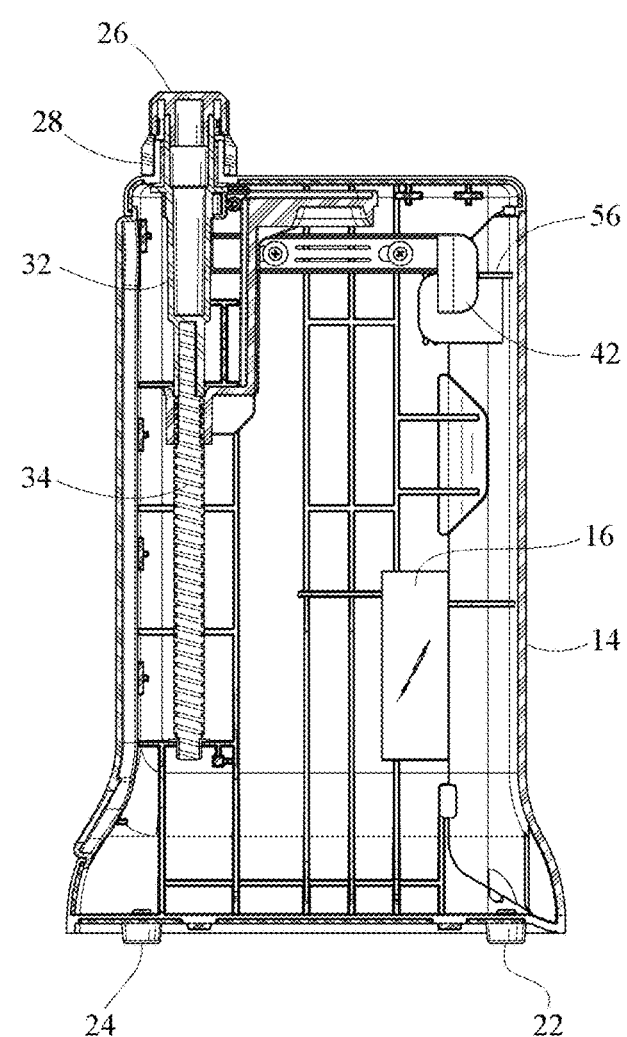
FIG. 7
FIG. 8

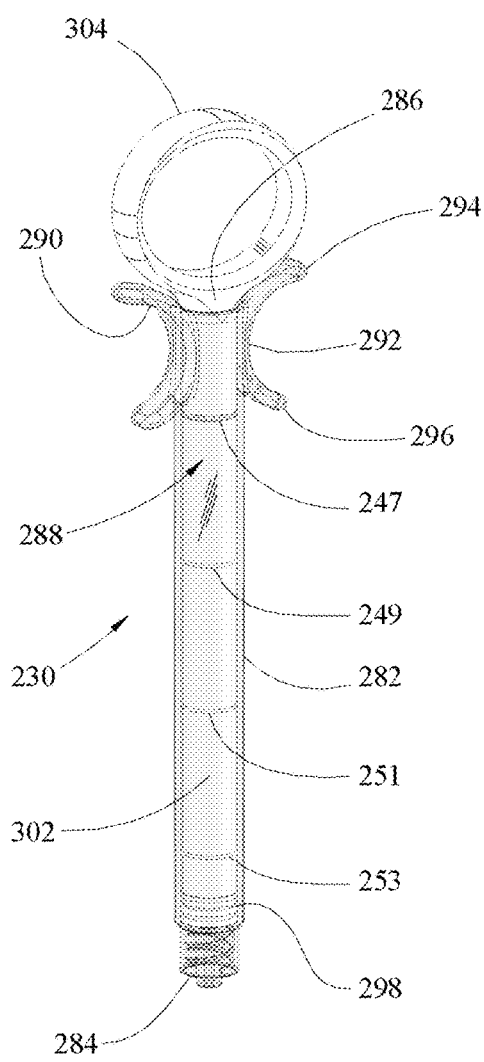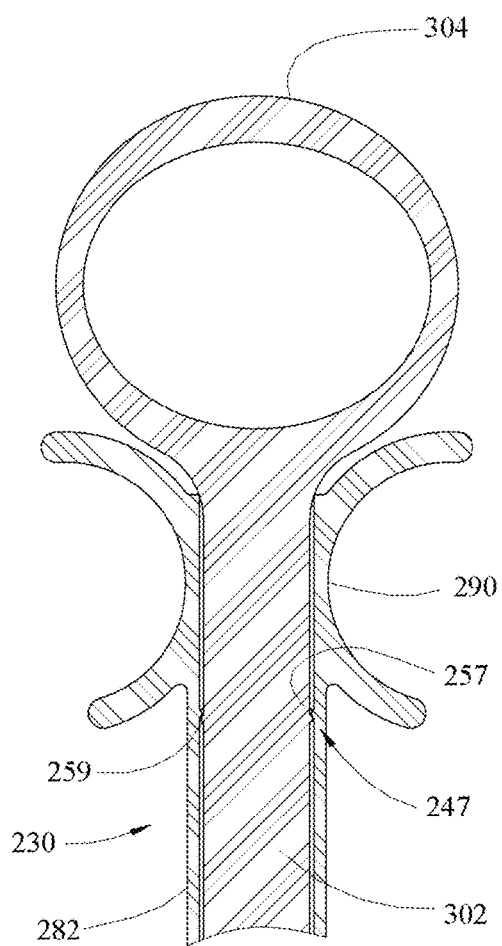
FIG. 22
FIG. 23

SYRINGE FILL SYSTEM AND METHOD

CROSS-REFERENCE TO RELATED APPLICATIONS

This is a continuation under 35 USC 120 of U.S. patent application Ser. No. 14/298,716 filed Jun. 6, 2014 in the names of Daniel K. Davidian, Scott G. Newnam, Eli B. Nichols, and Theodore J. Mosler for "Syringe Fill System and Method" and issued Jul. 12, 2016 as U.S. Pat. No. 9,387,151, which in turn claims benefit under 35 USC 119(e) of U.S. Provisional Patent Application No. 61/867,645 filed Aug. 20, 2013 in the name of Daniel K. Davidian for "Syringe Fill System and Method" and the benefit under 35 USC 119(e) of U.S. Provisional Patent Application No. 61/923,918 filed Jan. 6, 2014 in the names of Daniel K. Davidian, Scott G. Newnam, Eli B. Nichols, and Theodore J. Mosler for "Syringe Fill System and Method." The disclosures of U.S. patent application Ser. No. 14/298,716, U.S. Provisional Patent Application No. 61/867,645, and U.S. Provisional Patent Application No. 61/923,918 are hereby incorporated herein by reference, in their respective entireties, for all purposes.

FIELD

The present disclosure relates generally to liquid fill and mixing apparatus and methods, and more particularly to syringe fill systems, subassemblies, and components, syringes useful therewith, and methods of making and using the foregoing.

DESCRIPTION OF THE RELATED ART

In the use of syringes for medical procedures, in orthopedics, physical therapy, dentistry, dermatology, cosmetic surgery and many other fields of medical endeavor, it is desired to fill syringes with therapeutic fluids for administration to patients, at the point of use. Such point of use fill avoids monitoring and control of inventories of pre-filled packaged syringes, allows control of the amount of fluid that is provided in the syringe, and enables custom mixing of pharmaceutical composition ingredients, e.g., cocktail formulations of active pharmaceutical agents, to be provided at the time needed for administration to a patient.

Particularly in applications in which repeated injections must be administered, conventional fill operations are time-consuming and labor intensive, requiring close attention to the amount of fluid drawn into the chamber of the syringe as its plunger is retracted, as well as proper registration and/or coupling of the syringe to a fluid supply source in the first instance, and careful removal of the syringe from such fluid supply source after filling of the syringe. In instances in which multiple liquids are required, which must be mixed for administration, additional difficulties are present.

When such multiple liquids are involved, it is desired to mix them at the point of use in a manner that avoids degradation or impairment of liquid supplies, while at the same time achieving precision bulk filling of syringes, minimizing the incidence of needlestick events, minimizing the risk of errors, and increasing the efficiency and speed of preparation and subsequent injections.

In consequence, the art continues to seek improvements in syringe filling apparatus, as well as in syringes, and in associated processes and procedures.

SUMMARY

The present disclosure relates generally to liquid fill and mixing apparatus and methods, and more specifically to syringe fill systems and methods, syringe fill system subassemblies that may be provided as disposables for single-use products, and syringes Tillable by such syringe fill systems, subassemblies, and methods, as hereinafter more fully described.

In one aspect, the disclosure relates to a syringe fill system, comprising:
a housing in which is mounted a pusher arranged to exert downward pressure on a fluid supply package that is pressure-responsive to dispense fluid, the pusher being coupled with a track in the housing for bidirectional linear movement;
a selector and driver assembly operatively coupled with the pusher, arranged for user selection of an amount of a fluid to be dispensed and responsive to the user selection to translate the pusher against the fluid supply package for dispensing of the user-selected amount of the fluid, the selector and driver assembly including a pawl mechanism for limiting translation distance of the pusher to limit dispensing to the user-selected amount, as well as prohibit reverse motion of the pusher.

In another aspect, the disclosure relates to a cassette assembly, comprising:
a base manifold member including an interior manifold flow passage;
multiple fluid feed inlets extending outwardly from the base manifold member and communicating with the interior manifold flow passage via inlet passages containing check valves, the multiple inlets being configured for engagement with respective fluid supply packages; and
a syringe coupling mounted on the base manifold member, in fluid flow communication with the interior manifold flow passage to deliver fluid from the interior manifold flow passage to a syringe when coupled to the syringe coupling.

In a further aspect, the disclosure relates to a haptic and audible feedback syringe, comprising:
a barrel member defining an interior volume therein for receiving fluid for dispensing from the syringe in a dispensing operation, the interior volume being bounded by interior wall surface with a protrusion element on the interior wall surface at a proximal portion of the barrel member; and
a plunger configured for slidable engagement in the interior volume of the barrel member, wherein the plunger comprises an array of deformable flexible resilient finger elements in sequential longitudinally spaced-apart arrangement along a length of the plunger, the finger elements extending outwardly, transverse to a longitudinal axis of the plunger;
wherein the protrusion element and finger elements are dimensionally sized and positioned in relation to one another so that advancement of the plunger in the barrel member interior volume from a retracted position successively engages the finger elements with the protrusion so that contact resistance is transmitted by the plunger to a syringe user as a haptic feedback in initial contact of the finger and protrusion, with elastic deformation of the finger by the protrusion during subsequent advancement of the plunger and production of an audible output upon disengagement of the finger from the protrusion during such advancement. Such haptic feedback and audible output is also detected by the syringe user during plunger retraction from an advanced position.

In one aspect, the disclosure relates to a syringe fill system, comprising:

a syringe fill manifold including a manifold fill passage, an inlet for connection to a fluid supply assembly, and an outlet arranged to deliver fluid for syringe filling;

a fluid supply assembly adapted to receive a fluid container so that the fluid container is coupled to the inlet of the syringe fill manifold, with a one-way valve at the inlet to control flow of fluid from the fluid container to the manifold fill passage; and a dispensing assembly including a dispensing selector member operatively linked to a driver member arranged to control dispensing of fluid from the fluid container in an amount selectable by the dispensing selector member, wherein the fluid supply assembly and the dispensing assembly are arranged in side-by-side relationship with one another.

In another aspect of the disclosure relates to a syringe comprising a barrel defining an interior volume that is adapted for filling with a fluid, such syringe comprising in its interior volume a solid material that is solubilized or suspended when the syringe is filled with the fluid, to constitute a composition for administration by the syringe.

In a further aspect, the disclosure relates to a syringe comprising a syringe barrel defining an interior volume for holding fluid, a plunger member adapted for translational movement in the interior volume of the syringe barrel, and audible and kinesthetic feedback coaction structures, wherein the audible and kinesthetic feedback coaction structures comprise first protrusion structure on an interior surface of the barrel, and the plunger member comprises second protrusion structure engageable with the first protrusion structure to provide auditory and kinesthetic feedback during translational movement of the plunger member in the barrel of the syringe.

Yet another aspect of the disclosure relates to a syringe fill device for filling a syringe with a composition, comprising:
a fill station housing defining an interior volume therewithin;
a feed manifold mounted in the interior volume, such feed manifold including (i) passageways with inlets that are adapted to engage fluid carpules when mounted in the interior volume in flow communication with said inlets, and (ii) a syringe engagement port communicating with the passageways, and configured to mate with a distal end of a syringe body so that fluid flowing through the feed manifold flows into the syringe body;
a drive assembly adapted to be coupled with fluid carpules mountable in the interior volume, and arranged to effect fluid flow from at least one of the fluid carpules through the feed manifold to the syringe engagement port;
the housing being configured to receive the distal portion of a syringe body in the interior volume so that the distal end of the syringe body mates with the syringe engagement port of the feed manifold for filling of the syringe with fluid from one or more carpules mounted in the interior volume of the fill station housing.

In another aspect, the disclosure relates to a syringe fill device for filling a syringe with a composition, comprising:
a fill station housing defining an interior volume therewithin;
a feed manifold mountable in the interior volume, said feed manifold including (i) passageways with inlets that are adapted to engage fluid carpules when mounted in the interior volume in flow communication with said inlets, and (ii) a syringe engagement port communicating with said passageways, and configured to mate with a distal end of a syringe body so that fluid flowing through the feed manifold flows into the syringe body;
a drive assembly adapted to be coupled with fluid carpules mountable in the interior volume, and arranged to effect fluid flow from at least one of the fluid carpules through the feed manifold to the syringe engagement port;
the housing being configured to receive the distal portion of a syringe body in the interior volume so that the distal end of the syringe body mates with the syringe engagement port of the feed manifold for filling of the syringe with fluid from one or more carpules mounted in the interior volume of the fill station housing;
wherein the drive assembly comprises a motor drive assembly, comprising a separate motor coupled with a drive piston, for each fluid carpule mountable in the interior volume, wherein each separate motor and coupled drive piston is independently actuatable when the motor is powered, so that the drive piston is compressively engaged with a corresponding carpule to cause fluid from the carpule to flow through a passageway of the feed manifold to the syringe engagement port; and
wherein the feed manifold comprises an axially elongate leg, and angularly divergent legs, said angularly divergent legs each having a proximal end portion adapted for coupling with a distal end portion of a separate fluid carpule, and enclosing a divergent leg fluid flow passage, and said angularly divergent legs each having a distal end portion coupled to the axially elongate leg, wherein the axially elongate leg encloses two separate flow passages extending along the axially elongate leg, each separate flow passage being coupled to a respective one of the divergent leg fluid flow passages so that flows of fluids from separate carpules coupled to the feed manifold are not intermixed with one another in the axially elongate leg, and wherein the syringe engagement port comprises a one-way valve.

A further aspect the disclosure relates to a method of filling a syringe with fluid at a point of use, such method comprising use of a syringe fill system or syringe fill system subassembly of the present disclosure.

In a further aspect, the disclosure relates to a syringe fill assembly comprising a syringe fill device according to the present disclosure, and a syringe coupled at a distal end thereof to the syringe engagement port of the feed manifold for filling of the syringe with fluid.

A still further aspect of the disclosure relates to a therapeutic composition supply kit, comprising a syringe fill device according to the present disclosure, and at least one of components (A) and (B):

(A) syringes adapted to be coupled with the syringe fill device for filling thereof; and (B) carpules of the therapeutic composition or components thereof, adapted for installation in the syringe fill device and coupling with the feed manifold and the drive assembly.

In another aspect, the disclosure relates to a syringe fill system subassembly of a syringe fill system of the present disclosure.

A further aspect of the disclosure relates to a kit comprising such a syringe fill system subassembly, and a multiplicity of syringes adapted to be filled by the syringe fill system.

Other aspects, features and embodiments of the disclosure will be more fully apparent from the ensuing description and appended claims.

BRIEF DESCRIPTION OF THE DRAWINGS

FIG. 3 is an elevation view of a half-section of the housing of the syringe fill apparatus of FIG. 1, showing some of the internal components of the apparatus.

FIG. 4 is a plan cross-sectional view of a portion of the selector/driver assembly of FIG. 3.

FIG. 7 is a front elevation view of the syringe fill apparatus of FIGS. 1-6.

FIG. 8 is an elevation view of the half-section of the housing shown in FIG. 5, with the rear door installed to engage the pawl assembly with the cogwheel for fluid dispensing.

FIG. 22 is a perspective view of a syringe that is Tillable with the syringe fill system and subassembly of FIGS. 16-21.

FIG. 23 is a cross-sectional elevation view of the syringe of a portion of the syringe of FIG. 20, showing the details of the kinesthetic feedback features thereof.

DETAILED DESCRIPTION

Figure 1:
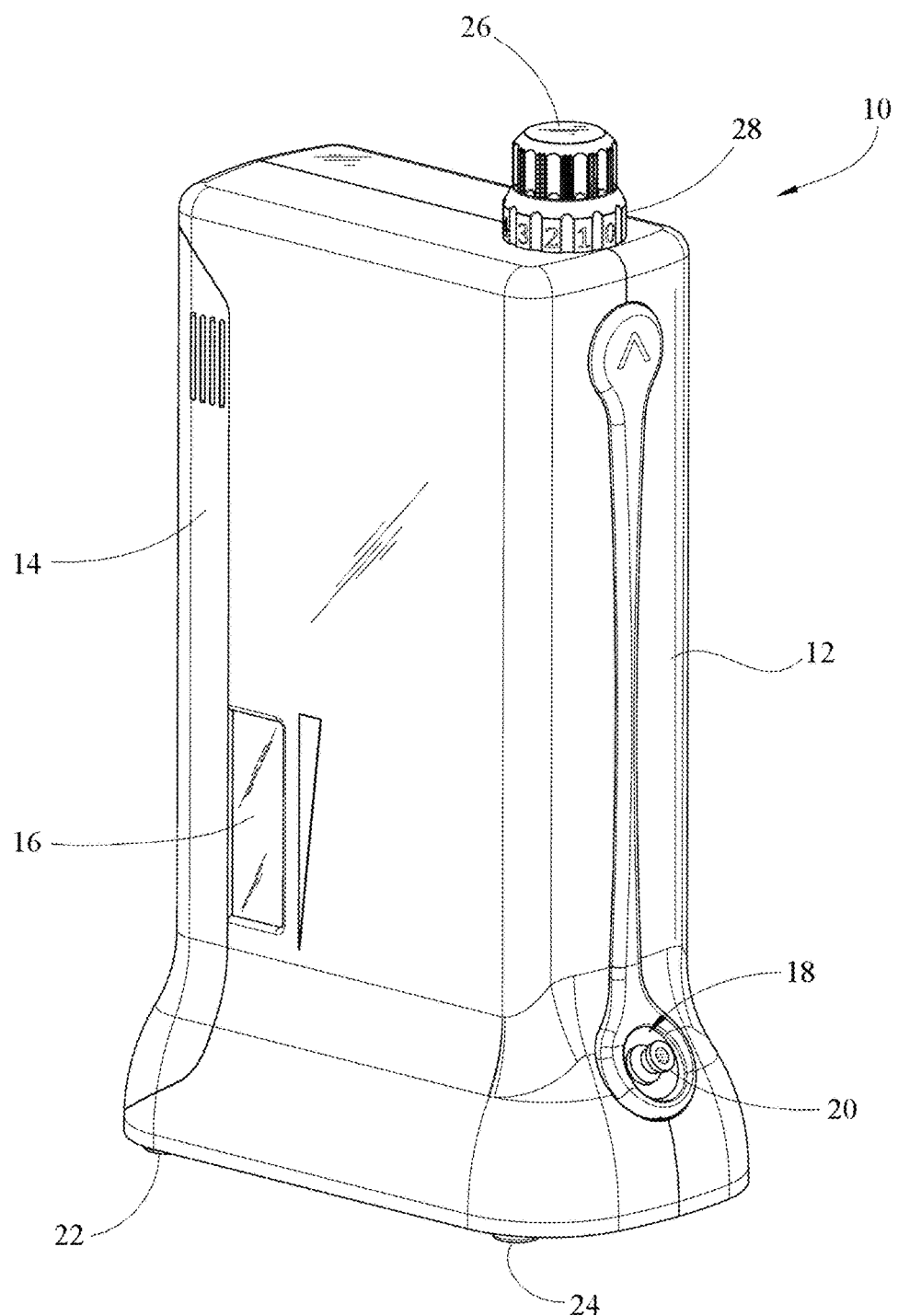
FIG. 1 is a perspective view of a syringe fill apparatus according to one embodiment of the present disclosure.

The present disclosure relates generally to liquid fill and mixing apparatus and methods, and more specifically relates to syringe fill systems and methods.

It will be recognized that the scope of the present disclosure is not limited by specific applications, and that the apparatus and methods described herein may be employed in a variety of implementations, e.g., in orthopedics, physical therapy, dentistry, dermatology, cosmetic surgery, and numerous other fields. Further, while the ensuing disclosure includes illustrative embodiments employing fluid sources for delivery and mixing of two separate fluids from respective source containers, it will be appreciated that the disclosure contemplates delivery and mixing of other numbers of multiple fluids from respective source containers, and that the apparatus and methods of the disclosure can be employed to deliver and mix 2, 3, 4, or more separate fluids from corresponding containers, e.g., vials, carpules, syringes, ampoules, etc.

The present disclosure contemplates syringe fill systems, subassemblies of such systems, syringes that can be filled using such fill systems or subassemblies, kits, and related methods.

In one aspect, the disclosure relates to a syringe fill system, comprising:

a housing in which is mounted a pusher arranged to exert downward pressure on a fluid supply package that is pressure-responsive to dispense fluid, the pusher being coupled with a track in the housing for bidirectional linear movement, e.g., with the track being disposed in a vertically extending or other orientation in the housing for bidirectional linear movement, e.g., bidirectional vertical linear movement;

a selector and driver assembly operatively coupled with the pusher, arranged for user selection of an amount of a fluid to be dispensed and responsive to the user to selection to translate the pusher against the fluid supply package for dispensing of the user-selected amount of the fluid, the selector and driver assembly including a pawl mechanism for limiting translation distance of the pusher to limit dispensing to the user-selected amount, as well as prohibit reverse motion of the pusher. The pawl mechanism advantageously is arranged to restrict reverse rotation of the selector and driver assembly when engaged.

In another aspect, the disclosure relates to a cassette assembly, comprising:

a base manifold member including an interior manifold flow passage;

multiple fluid feed inlets extending outwardly from the base manifold member and communicating with the interior manifold flow passage via inlet passages containing check valves, the multiple inlets being configured for engagement with respective fluid supply packages; and a syringe coupling mounted on the base manifold member in fluid flow communication with the interior manifold flow passage to deliver fluid from the interior manifold flow passage to a syringe when coupled to the syringe coupling. The multiple fluid feed inlets may extend outwardly, e.g., upwardly, from the base manifold member on an upper surface thereof, and the syringe coupling may be mounted on such upper surface of the base manifold member. Such multiple fluid feed inlets may for example be vertically extended in orientation.

In a further aspect, the disclosure relates to a haptic and audible feedback syringe, comprising:

a barrel member defining an interior volume therein for receiving fluid for dispensing from the syringe in a dispensing operation, the interior volume being bounded by interior wall surface with a protrusion element on the interior wall surface at a proximal portion of the barrel member; and a plunger configured for slidable engagement in the interior volume of the barrel member, wherein the plunger comprises an array of deformable flexible resilient finger elements in sequential longitudinally spaced-apart arrangement along a length of the plunger, the finger elements extending outwardly, transverse to a longitudinal axis of the plunger;

wherein the protrusion element and finger elements are dimensionally sized and positioned in relation to one another so that advancement of the plunger in the barrel member interior volume from a retracted position successively engages the finger elements with the protrusion so that contact resistance is transmitted by the plunger to a syringe user as a haptic feedback in initial contact of the finger and protrusion, with elastic deformation of the finger by the protrusion during subsequent advancement of the plunger and production of an audible output upon disengagement of the finger from the protrusion during such advancement. Such haptic feedback and audible output is also detected by the syringe user during plunger retraction from an advanced position.

One aspect of the disclosure relates to a syringe fill system, comprising:

a syringe fill manifold including a manifold fill passage, an inlet for connection to a fluid supply assembly, and an outlet arranged to deliver fluid for syringe filling;

a fluid supply assembly adapted to receive a fluid container so that the fluid container is coupled to the inlet of the syringe fill manifold, with a valve at the inlet to control flow of fluid from the fluid container to the manifold fill passage; and a dispensing assembly including a dispensing selector member operatively linked to an actuator member arranged to control dispensing of fluid from the fluid container in an amount selectable by the dispensing selector member, wherein the fluid supply assembly and the dispensing assembly are arranged in side-by-side relationship with one another.

In such syringe fill system, the fluid supply assembly may be adapted to receive a fluid container so that the fluid container is positioned above the syringe fill manifold, in the aforementioned site-by-side relationship with the dispensing assembly. When the syringe fill system is utilized with a syringe providing haptic feedback and audible output, and the syringe fill system utilizes a vented vial adapter, the syringe user is able to pull/aspirate fluid from the vial with guidance from the haptic feedback and audible output, as the syringe plunger is retracted from an advanced position. A vented vial adapter facilitates connection to a large volume source, such as a 50 mL vial.

In various embodiments of such syringe fill system, as hereinafter more fully described, the dispensing selector member in the dispensing assembly is operatively linked via compression and torsional springs with the actuator member, and the actuator member is arranged for downward, e.g., vertical downward, travel on a lead screw in response to rotational movement of the dispensing selector member followed by downward translation of the dispensing selector member, with the actuator member during downward translation on the lead screw causing fluid to flow from the fluid container to the manifold fill passage of the syringe fill manifold, and with the compression spring acting to return the dispensing selector member to a starting position after the amount of fluid selected by the dispensing selector member has been flowed from the fluid container to the manifold fill passage of the syringe fill manifold.

In the syringe fill systems as variously described above, the dispensing selector member can be fabricated and arranged so that it is rotatable to cause display of a corresponding selected amount of fluid and the torsional spring as described above can be configured to cause the display to reset to an initial state upon depression of the selector member.

The syringe fill systems of the disclosure may be constituted, so that the fluid supply assembly is adapted to receive at least one additional fluid container so that each such additional fluid container is positioned above the syringe fill manifold and is coupled to a corresponding additional inlet of the syringe fill manifold, with a one-way valve at each such additional inlet to control flow of fluid from the corresponding additional fluid container to the manifold fill passage. In the syringe fill system, the fluid supply assembly may be adapted to receive a second fluid container so that the second fluid container is positioned above the syringe fill manifold.

Such a syringe fill system may be provided, as adapted for push-pull dispensing of fluids from first and second fluid containers, e.g., with the one-way valves at the inlets of the syringe fill manifold comprising check valves of different crack pressure character. In specific embodiments, the check valve for push dispensing of fluid from the first fluid container has a crack pressure that is in a range of from 6 to 20 psi, and the check valve for pull dispensing of fluid from the second fluid container has a crack pressure that is in a range of from 0.5 to 10 psi, with the proviso that the crack pressure of the check valve for push dispensing is greater than the crack pressure of the check valve for pull dispensing.

Such a system is advantageously employed, as further comprising a first fluid container of buffering medium and a second fluid container of anesthetic composition in the fluid supply assembly. The buffering medium may for example comprise sodium bicarbonate, and the anesthetic composition may comprise lidocaine, articaine, or marcaine.

In various embodiments, the syringe fill system as above described may further comprise a housing in which the syringe fill manifold, the fluid supply assembly, and the dispensing assembly are mounted.

Such a syringe fill system may be fabricated, with the housing including one or more syringe coupling ports in which is disposed a syringe coupling that is connected in fluid flow communication with the outlet of the syringe fill manifold or separate liquids. The housing may additionally include a viewing port adapted for viewing of a displayed fluid amount that has been selected using the dispensing selector member, for dispensing in the syringe filling. In other embodiments, the housing may include a viewing window for viewing a fluid inventory in a fluid container in the fluid supply assembly. The syringe fill system may employ a dispensing selector member of the dispensing assembly, which comprises a manual selector knob that is located outside the housing, as hereinafter more fully described.

The syringe fill system may be constructed, with the dispensing assembly and the fluid supply assembly being generally vertically extending in orientation, as provided in side-by-side relationship to one another, thereby providing a highly compact and efficient arrangement of the system and ensuring that any air contained in the fluid containers remains atop the fluid inventory so that the syringe fill manifold remains primed and free of air.

The syringe fill system of the disclosure may be adapted for manual operation, automated operation, or a combination of manual and automatic operation.

With respect to "push" and "pull" fluid dispensing modalities, as hereinafter more fully described, the syringe fill system may be adapted for push-push dispensing of fluids, pull-pull dispensing of fluids, push-pull dispensing of fluids, or pull-push dispensing of fluids, as will be appreciated in the context of the ensuing disclosure. In general, with any number of different fluids being accommodated by the syringe fill system in various embodiments, each of the different fluids may be independently dispensed to a syringe via either push dispensing or alternatively by pull dispensing.

As used herein, a "push" mode of fluid filling describes the movement of fluid as a result of positive pressure applied to the fluid, e.g., during compression of a syringe plunger in a barrel of the syringe, and a "pull" mode of fluid filling describes the movement of fluid as a result of negative pressure applied to the fluid, e.g., during the aspiration or withdrawal of a syringe plunger in a barrel of the syringe.

In specific configurations, the syringe fill system may comprise a fluid supply container sleeve adapted to receive a fluid container including a pierceable cap or cover, with the container sleeve including a piercing member for piercing the pierceable cap or cover, and an air inletting vent enabling air to enter the container to facilitate dispensing of fluid from the fluid supply container. Such air inletting vent may include a hydrophobic filter effective to remove airborne contaminants that may adversely affect fluid supplied by the fluid supply container.

The syringe fill system may be arranged with a syringe coupling that is connected in fluid flow communication with the outlet of the syringe fill manifold, and the syringe coupling may be adapted to be swabable for cleaning and/or sterilization thereof.

The disclosure relates in another aspect to a syringe fill system subassembly of the syringe fill system of the disclosure. The syringe fill system subassembly may comprise the syringe fill manifold and the fluid supply assembly, or other permutations or combinations of syringe fill system components. The subassembly may be adapted to receive additional fluid containers so that each such additional fluid container is positioned above the syringe fill manifold and is coupled to a corresponding additional inlet of the syringe fill manifold, with a one-way valve at each such additional inlet to control flow of fluid from the corresponding additional fluid container to the manifold fill passage.

For example, the subassembly may be constructed, so that it is adapted to receive a second fluid container, with the second fluid container positioned above the syringe fill manifold, to provide for fluid mixing of the first and second fluids to form a multicomponent fluid that then is used to fill the syringes.

As in the case of the syringe fill system, the syringe fill subassembly may be adapted for push-pull dispensing of fluids from first and second fluid containers. The valves at the inlet of the syringe fill manifold for such purpose may comprise check valves of different crack pressure character.

As previously described, the check valve for push dispensing of fluid from the first fluid container may have a crack pressure that is in a range of from 6 to 20 psi, and the check valve for pull dispensing of fluid from the second fluid container may have a crack pressure that is in a range of from 0.5 to 10 psi, with the proviso that the crack pressure of the check valve for push dispensing is greater than the crack pressure of the check valve for pull dispensing.

Like the syringe fill system, the subassembly may be adapted for manual and/or automated operation, in any combination of push and/or pull modalities of fluid dispensing.

The syringe fill system subassembly, like the previously described syringe fill system, can comprise a fluid supply container sleeve adapted to receive a fluid container including a pierceable cap or cover, with the container sleeve including a piercing member for piercing the pierceable cap or cover, and an air inletting vent enabling air to enter the container to facilitate dispensing of fluid from the fluid supply container. The vent as previously described may comprise a hydrophobic filter that is effective to remove airborne contaminants that may adversely affect fluid supplied by the fluid supply container.

The subassembly may further comprise a syringe coupling that is connected in fluid flow communication with the outlet of the syringe fill manifold. The coupling may be constructed and arranged, so that it is adapted to be swabable for cleaning and/or sterilization thereof.

The syringe fill system subassembly may also be provided as a disposable unit, e.g., fabricated predominately of plastic and elastomeric material(s) of construction, or otherwise constructed and arranged for disposable or single-use character. Further, the plastic and elastomeric materials may be sterilizable by various methods such as ethylene oxide gas or radiation.

A further aspect of the disclosure relates to a kit including (i) the above-described syringe fill system subassembly (which then may be installed in the housing including a dispensing assembly adapted to engage cooperatively with the subassembly), and optionally (ii) a multiplicity of syringes adapted to be filled by the syringe fill system. The syringes may be of any suitable type, and may for example comprise kinesthetic feedback (haptic feedback and audible output) coaction structures.

Syringes useful in the broad practice of the present disclosure include syringes comprising a barrel defining an interior volume that is adapted for filling with a fluid, in which the syringe includes in its interior volume a solid material, e.g., a particulate solid material, that is solubilized or suspended when the syringe is filled with the fluid, to constitute a composition for administration by the syringe. The solid material may comprise a buffering agent such as sodium bicarbonate, or other solid material useful to make up a fluid formulation for subsequent administration by the syringe.

The syringes utilized with the syringe fill system may comprise kinesthetic feedback coaction structures. The kinesthetic feedback coaction structures may be of any suitable type, and in various embodiments may include first protrusion structure on an interior surface of the barrel. The syringe in such construction may include a plunger member having on a surface thereof second protrusion structure engageable with the first protrusion structure to provide kinesthetic feedback during translational movement of the plunger member in the barrel of the syringe.

The kinesthetic feedback coaction structures may comprise multiple elements of the first protrusion structure, in which each of the multiple elements of the first protrusion structure is disposed on the interior surface of the barrel, in spaced-apart relationship to other(s) of the multiple elements of the first protrusion structure. Successive ones of the multiple elements of the first protrusion structure may be spaced apart at intervals along the interior surface of the barrel, so that such elements demarcate injection volumes of fluid to be administered by the syringe.

Alternatively, the kinesthetic feedback coaction structures may comprise multiple elements of the second protrusion structure on the plunger member of the syringe, which are engageable with the first protrusion structure on an interior surface of the barrel of the syringe.

In another aspect, the disclosure contemplates a method of filling a syringe with fluid at a point of use, in which the method comprises use of an above-described syringe fill system or syringe fill system subassembly. Such method may be carried out with a composition comprising anesthetic, e.g., an anesthetic selected from among lidocaine, articaine, and marcaine. The composition may further comprise buffering medium, and the respective anesthetic and buffering medium may be supplied to the syringe fill manifold from separate anesthetic and buffer medium supply containers mounted in the fluid supply assembly, to form a buffered anesthetic composition for filling of the syringe. As previously described, the buffering medium may be supplied to the syringe fill manifold in a push mode of dispensing from a buffering medium supply container, and the anesthetic may be supplied to the syringe fill manifold in a pull mode of dispensing from an anesthetic supply container.

More generally, the syringe may be filled with a composition comprising components supplied from different supply containers mounted in the fluid supply assembly, in various push and/or pull modes of fluid dispensing of respective components.

Referring now to the drawings, FIG. 1 is a perspective view of a syringe fill apparatus 10 according to one embodiment of the disclosure. The fill apparatus 10 includes housing 12. The front face of the housing at its lower portion includes a syringe coupling port 18 in which is disposed a syringe coupling 20.

At its rear portion, the housing 12 includes a removable rear door 14, permitting access to internal components in the interior volume of the housing. The rear portion of the housing also includes a window 16, permitting visual verification of the fluid inventory in a fluid supply container in the housing interior volume. The housing 12 is provided on its bottom face with rear bumper feet 22 and front bumper feet 24, which may be made of rubber or other elastomer material. At its upper portion, the housing includes a dispensing assembly including rotary knob 26 and detent knob 28, the function and operation of which are hereinafter more fully described.

Figure 2:
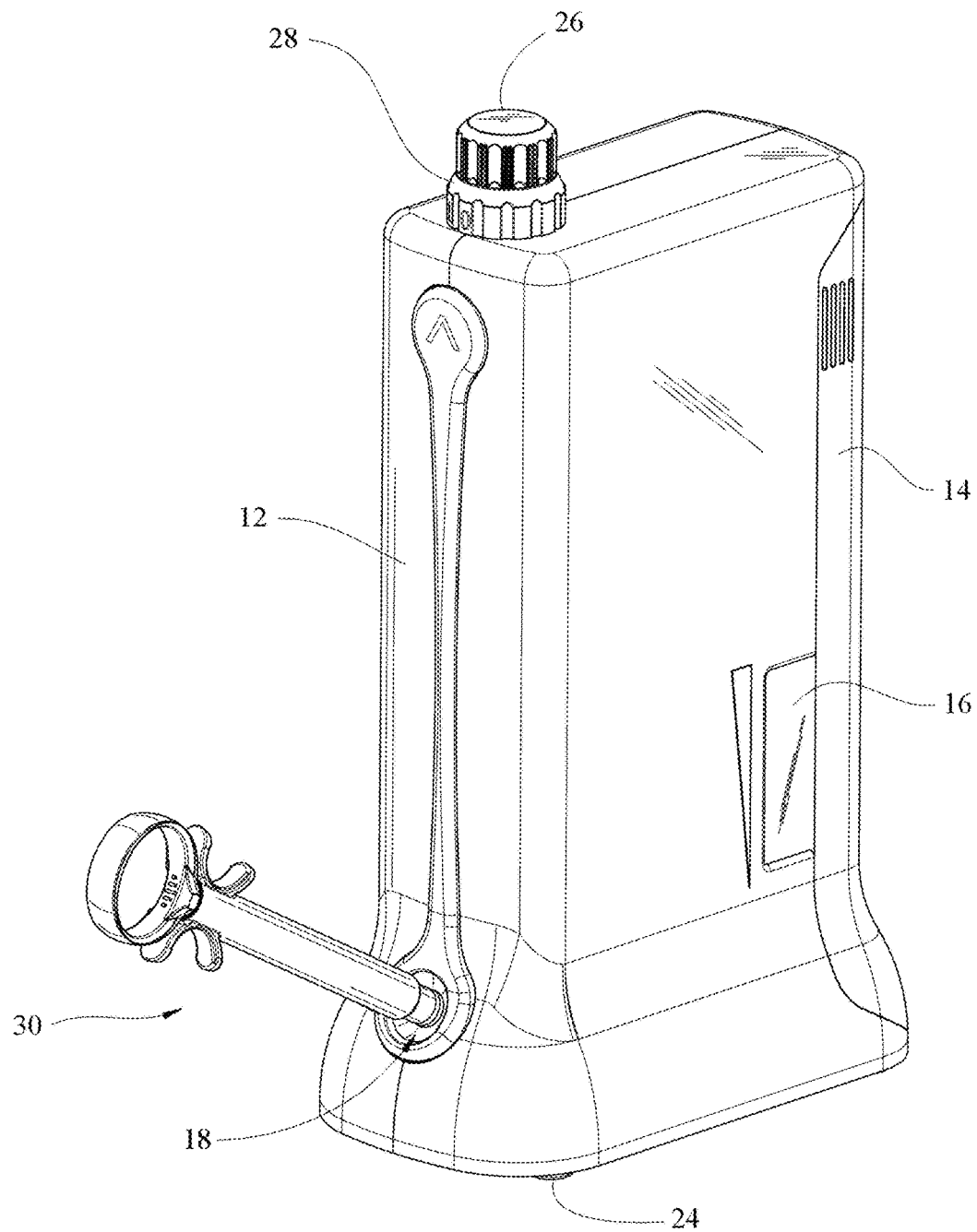
FIG. 2 is a perspective view of the syringe fill apparatus of FIG. 1, coupled with a syringe for filling thereof.

FIG. 2 is a perspective view of the syringe fill apparatus of FIG. 1, coupled with a syringe for filling thereof. As illustrated, a syringe 30 is shown as being coupled with the syringe coupling in the syringe coupling port 18 of the syringe fill apparatus.

FIG. 3 is an elevation view of a half-section of the housing of the syringe fill apparatus of FIG. 1, showing some of the internal components of the apparatus. FIG. 3 is numbered correspondingly to FIGS. 1 and 2, with respect to corresponding parts and features thereof.

As illustrated in FIG. 3, a selector/driver assembly comprises a rotary knob 26 overlying a detent knob 28 on a front top surface of the housing 12. The knobs are cooperatively arranged with respect to a drive shaft 32 that in turn is coupled to a lead screw 34, being coaxial with one another, as shown in FIG. 4, which is a plan cross-sectional view of the corresponding portion of the selector/driver assembly of FIG. 3.

The selector/driver assembly as shown in FIG. 3 further includes a pusher 36 which is engaged with the drive shaft 32 and a lead screw 34, as shown. The pusher includes a rearwardly extending flange having a lower bearing surface arranged to exert a downward pressure on a first fluid container to dispense same, as the pusher is downwardly translated in response to the user selection made by rotation of the rotary knob 26, directly transmitted to lead screw 34. Prior to turning rotary knob 26, the user may dial the selected dose on the detent knob 28, with the rotary knob 26 remaining stationary. Then, during subsequent rotation of the rotary knob 26, the detent knob 28 follows the rotary knob 26, counting down from the selected dose to zero. For such purpose, the pusher 36 is mounted on a carriage (in an arrangement not shown in FIG. 3, but wherein the pusher is secured to the carriage by the four Phillips-head screws illustrated in FIG. 3). The pusher in such arrangement is translatable, e.g., vertically translatable, along the pusher rail 38 during the first fluid dispensing operation. The pusher rail 38 is secured to the housing by means of mechanical fasteners, e.g., the mechanical fastener 40 shown at the lower portion of the pusher rail.

Figure 6:
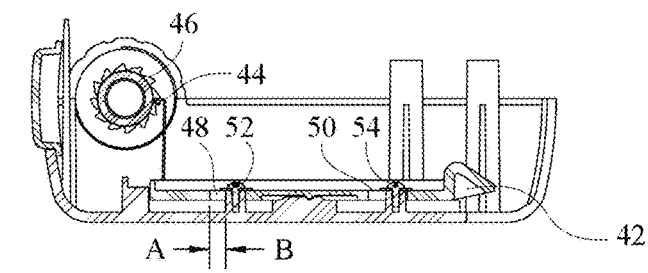
FIG. 6 is a sectional plan view of the apparatus of FIG. 5, taken along line 6-6.
Figure 5:
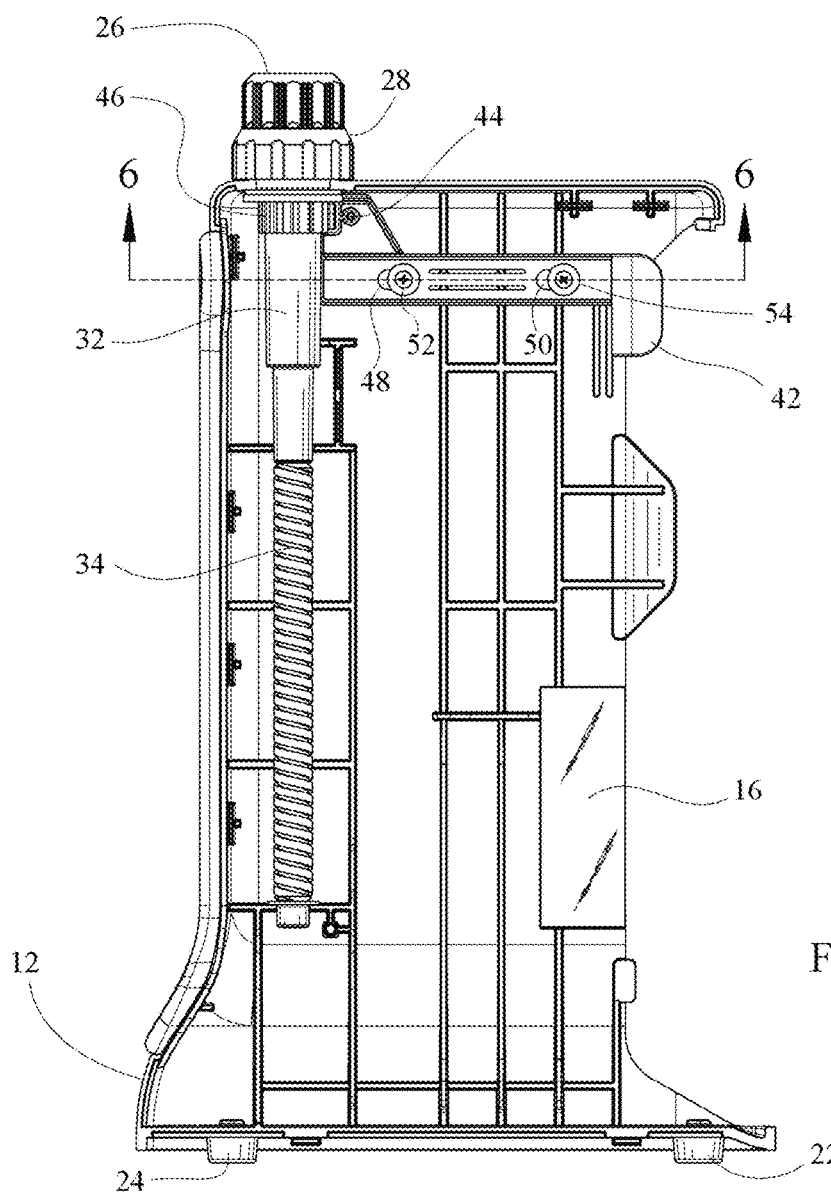
FIG. 5 is an elevation view of a half-section of the housing that is complementary to the half-section illustrated in FIG. 3 and that shows details of the pawl assembly for dispensing a first fluid.

FIG. 5 is an elevation view of a half-section of the housing that is complementary to the half-section illustrated in FIG. 3 and that shows details of the pawl assembly for dispensing a first fluid. Corresponding parts and features in FIG. 5 are numbered correspondingly to the same parts and features in FIGS. 1-4. FIG. 6 is a sectional plan view of the apparatus of FIG. 5, taken along line 6-6.

As illustrated in FIGS. 5 and 6, a slidable pawl member 42 comprising elongate slots 48 and 50 is slidably coupled with posts disposed in the slots, and with the pawl member being positionally retained by retention screws 52 and 54 having washers associated therewith. The posts are integrally formed with the wall of the housing half-section. The slidable pawl member 42 on a front portion thereof has a pawl arm 44 mounted thereon, arranged so that when the slidable pawl member is forwardly advanced, the pawl arm 44 engages the geared surface of the cogwheel 46 at a position determined by the rotation of the rotary knob 26.

As shown, the detent knob 28 on its exterior circumferential surface has a series of numbers corresponding to the corresponding number of volumes of fluid that is to be dispensed to the syringe in the dispensing operation. In this manner, the specific volume to be dispensed can be selected, so that the drive shaft 32 is actuated by the rotary knob 26 to rotate the lead screw. In this manner the pusher 36, by action of the drive shaft and lead screw, is advanced downwardly by a corresponding amount, to dispense the desired volume of first fluid to the dispensing manifold, as hereinafter more fully described.

FIG. 7 is a front elevation view of the syringe fill apparatus of FIGS. 1-6, and is numbered correspondingly to FIGS. 1-6. FIG. 8 is an elevation view of the half-section of the housing shown in FIG. 5, and as taken along line 8-8 of FIG. 7, with the rear door 14 closed to engage the pawl assembly with the cogwheel for fluid dispensing. Specifically, the rear door 14 has a rear door tab 56 that when the rear door is closed urges the slidable pawl member 42 forwardly to engage the cogwheel, so that dispensing of a predetermined volume of the first fluid can be carried out.

Figure 9:
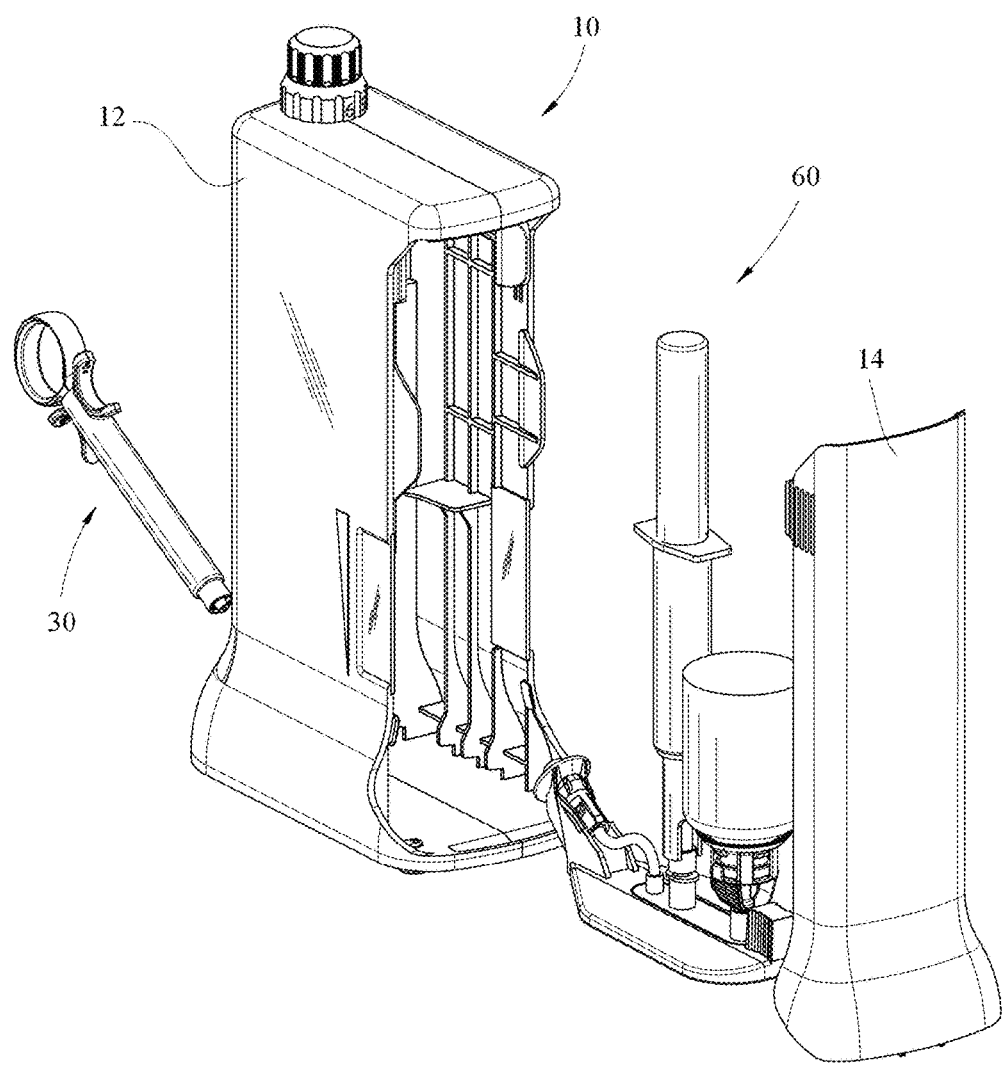
FIG. 9 is an exploded view of a syringe fill system according to one embodiment of the present disclosure, showing a cassette assembly as installed in the housing of the syringe fill apparatus, and a syringe for coupling with the syringe coupling in the syringe coupling port of the syringe fill apparatus.

FIG. 9 is an exploded view of a syringe fill system according to one embodiment of the present disclosure, showing a cassette assembly 60 as installed in the housing of the syringe fill apparatus 10, and a syringe 30 for coupling with the syringe coupling in the syringe coupling port of the syringe fill apparatus. As assembled, the cassette assembly 60 is positioned in the interior volume of the housing 12. The rear door 14 is secured to the housing 12 to enable the slidable pawl member to engage the cogwheel of the selector/dispensing assembly and enable selection of the fluid volume to be dispensed, and dispensing thereof.

Figure 10:
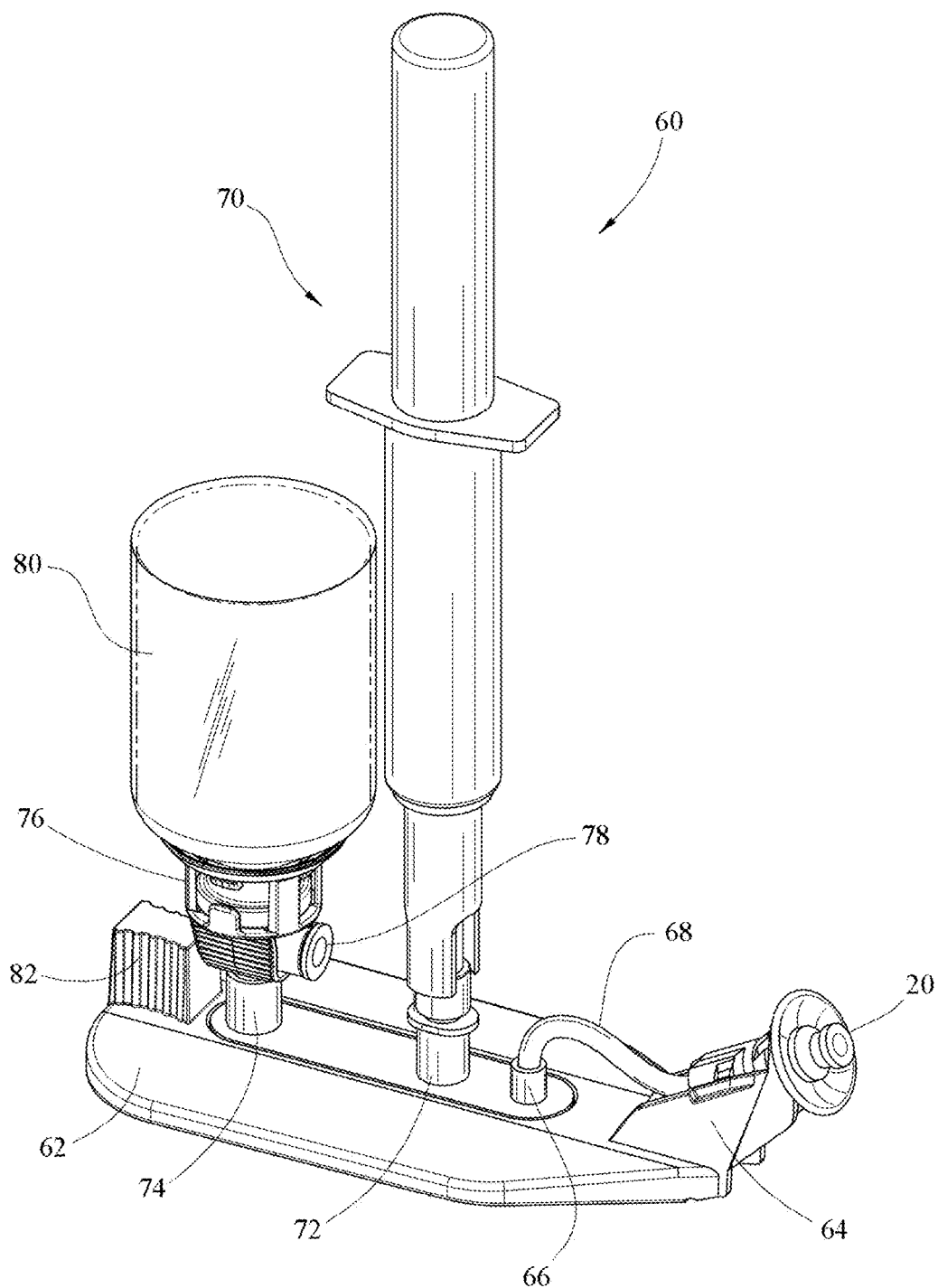
FIG. 10 is a perspective view of a cassette assembly according to one embodiment of the present disclosure.

FIG. 10 is a perspective view of a cassette assembly 60 according to one embodiment of the present disclosure.

The cassette assembly 60 includes a manifold 62 serving as a base member for the assembly. A syringe engagement support 64 is provided at a front end portion of the manifold. The syringe coupling 20 is mounted on the syringe engagement support 64. The manifold 62 includes a manifold fluid outlet 66 for discharging fluid from the manifold's interior flow passage, as hereafter described. A manifold discharge line 68 interconnects the syringe coupling 20 with the manifold fluid outlet 66 for delivering mixed fluid from manifold to a syringe when coupled with the syringe coupling.

The manifold 62 further includes a first fluid supply assembly 70 that is coupled with the manifold at the first fluid manifold inlet 72. Such coupling may be effected by complementary threading on the distal portion of the first fluid supply assembly and the inlet 72, to enable threaded engagement thereof. Alternatively, the coupling may be effected by snap-fit couplings, by luer lock connection, or in any other suitable manner.

The first fluid supply assembly 70 is suitably of a type involving an upper portion that is downwardly slidable against the a lower portion to effect dispensing of contained fluid, e.g., a fluid injector such as an Abboject® injector (commercially available from Hospira, Inc., Lake Forest, Ill., USA), a syringe, a carpule or other fluid package from which fluid can be dispensed by exertion of pressure thereon, so that the downward translation of the pusher on the fluid package causes fluid to be dispensed from the package to the manifold. It is to be noted that there is no introduction of air to the first fluid supply assembly during the dispensing of its contents, which provides the benefit of protecting the contents from degradation as potentially caused by introduction of air. This is especially beneficial to fluids such as sodium bicarbonate solutions.

The manifold 62 also includes a second fluid manifold inlet 74 to which is secured a vial adapter 76, as a coupling structure for the second fluid vial 80 shown in FIG. 10. The vial adapter may be of any suitable type, as effective to provide fluid flow communication with a source container of a second fluid. The vial adapter 76 may for example comprise a Vialok® vented vial access adapter, commercially available from Yukon Medical (Durham, N.C., USA) including a shrouded spike for piercing a closure member of a standard drug vial, e.g., a standard 13 mm, 20 mm, or 28 mm vial. Other vial connectors may be employed, which utilize a piercing or opening member or mechanism. Preferably, such fluid supply container connection enables the fluid supply container to be inverted in position above the second fluid inlet to facilitate gravitational feeding of fluid. The vial adaptor shown in FIG. 10 provides a vial adapter air inletting vent 78 to prevent vapor lock or other conditions that would interfere with the free flow of fluid from the coupled second fluid vial.

The vial adapter may be secured to the second fluid manifold inlet 74 in any appropriate manner. For example, it may be threadably engaged with the inlet 74, luer-lock coupled, snap-fit connected, or it may be adhesively bonded or mechanically secured to the inlet.

The manifold 62 is provided with a manual gripping element 82, to enable the cassette assembly to be manually grasped and guided into position when the cassette assembly is inserted into the housing of the syringe fill apparatus, or otherwise removed upon depletion of contents from fluid source containers.

It will be recognized that the cassette assembly, although shown in FIG. 10 as including a first fluid supply assembly 70 and a second fluid vial 80, may alternatively be commercially provided as a product assembly that does not include such fluid source components, and that the first fluid supply assembly 70 and a second fluid vial 80 may be separately sold or packaged. For example, the cassette assembly, without such fluid source components, may be formed of plastic and elastomeric or other disposable material, so as to be wholly disposable or recyclable in character. In various embodiments, the cassette assembly may be packaged and sold as a disposable unit, e.g., wherein the cassette assembly is fabricated predominantly (such as greater than 50% by weight of the assembly) of sterilizable plastic material(s) of construction, or otherwise configured as a disposable or single-use product.

Alternatively, the cassette assembly can be formed of a steam-sterilizable (autoclavable) character, so as to be reusable in character.

The cassette assembly thus may be packaged and sold with fluid source components, as a kit of the respective parts, or the cassette assembly itself without such fluid source components may be sold as a separate product article, or the cassette assembly including fluid source components installed therein for use, may be sold as an immediately usable product.

Figure 11:
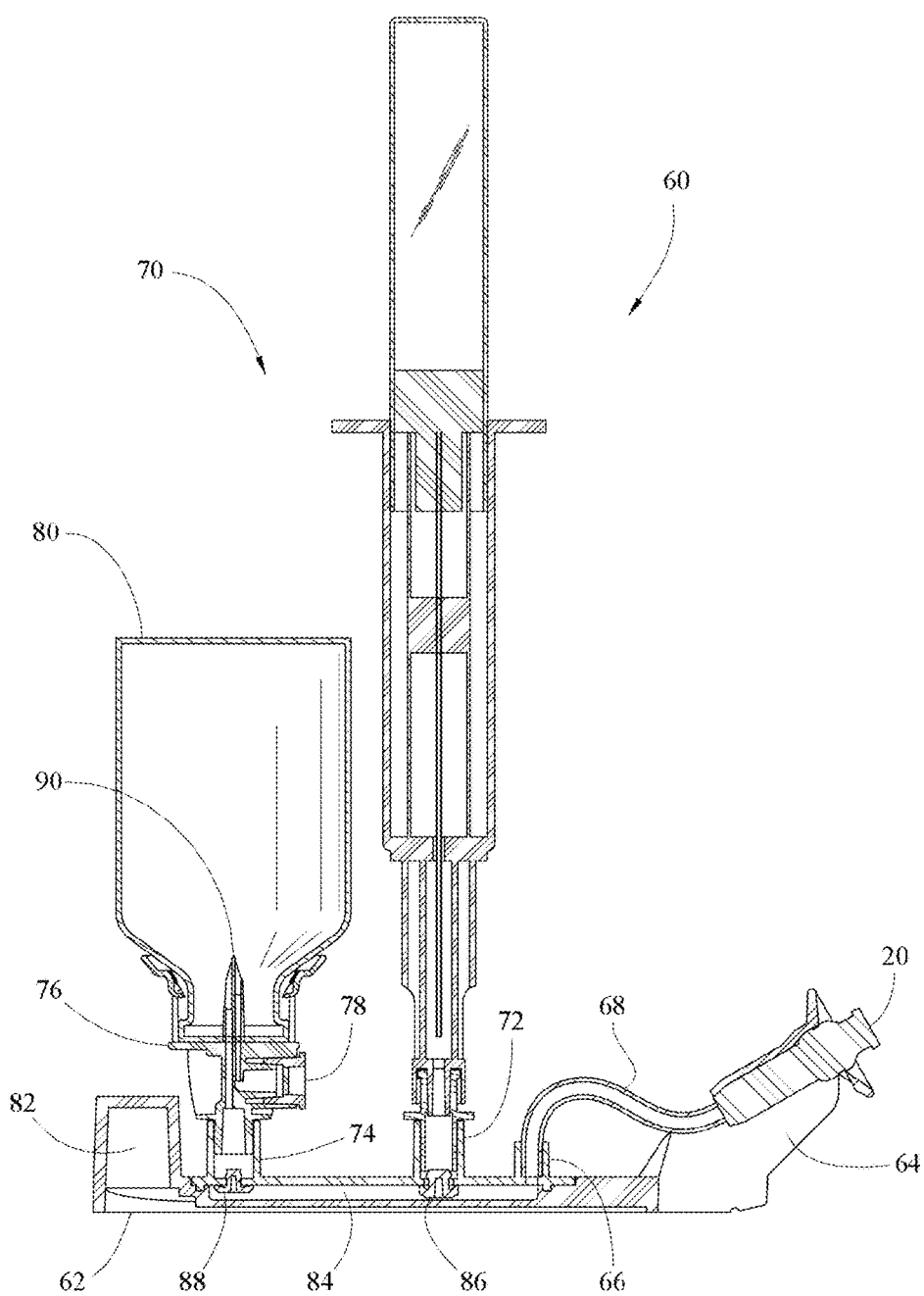
FIG. 11 is a side elevation view of the cassette assembly of FIG. 10, showing the details of construction thereof.

FIG. 11 is a side elevation view of the cassette assembly of FIG. 10, including fluid source components coupled therewith, showing the details of construction thereof. The respective parts and components of the cassette assembly are numbered correspondingly with respect to the numbering of the corresponding elements in FIG. 10. As illustrated in FIG. 11, the manifold 62 defines a manifold flow passage 84, having the first fluid manifold inlet 72 and the second fluid manifold inlet 74 coupled thereto, the manifold being provided with first fluid supply check valve 86 and second fluid supply check valve 88 in the respective inlets, to modulate one-way flow of the first and second fluids into the manifold flow passage from the first fluid supply assembly 70 and second fluid supply vial 80, respectively.

The second fluid supply vial 80 as illustrated is engaged with the vial adapter 76 so that the spike member 90 pierces the cap or cover of the vial when the vial is coupled with the vial adapter. The vial adapter air inletting vent 78 enables air to enter the vial 80 to facilitate dispensing of fluid from the vial. The air inletting vent may comprise a suitable hydrophobic filter effective to remove airborne contaminants that might otherwise adversely affect the second fluid. For example, a 0.2 μm filter may be employed to maintain fluid in the second fluid supply container in a sterile condition, while enabling efficient dispensing of fluid from such container to be carried out.

The manifold fluid outlet 66 is coupled with a manifold discharge line 68 that communicates with the syringe coupling 20. The syringe coupling 20 is mounted on syringe engagement support 64, and the syringe coupling may be oriented on such support at any suitable angle desired for coupling with a syringe to be filled by the syringe fill system. Syringe coupling 20 may be a luer-activated valve, such as the SmartSite® Needle-free Valve, commercially available from CareFusion Corp. (San Diego, Calif., USA) or a similar multi-access connector.

The cassette assembly shown in FIGS. 10 and 11 is adapted to be installed in the housing illustrated in FIGS. 1-9, and can be supplied as a unitary subassembly, e.g., as a disposable unit that may be utilized for fluid filling of syringes from a set of first and second fluid containers, and then discarded for recycling or other disposition.

The second fluid supply vial in the FIGS. 1-11 system can be utilized for dispensing of a second fluid from the vial in a "draw" or "pull" mode, in which a syringe is coupled with the syringe coupling 20 of the cassette assembly, and the plunger of the syringe is retracted to flow the second fluid from the second fluid supply vial through second fluid manifold inlet 74, into and through the manifold flow passage 84 to the syringe. For such purpose, the second fluid supply check valve 88 should have a "crack pressure"—i.e., the pressure at which the check valve will open to accommodate flow therethrough—that accommodates such pull mode of syringe filling.

In various applications, it may be desired to operate the syringe fill system of the type illustrated in FIGS. 1-11 so that one of the fluid supply check valves 86 and 88 is closed while the other one of such valves is open, and the respective valves for such purpose may have different crack pressure ratings to accommodate the desired dispensing operation.

The syringe fill system illustrated in FIGS. 1-11 can be utilized in various dental applications, in which the first fluid is dispensed into the manifold flow passage by the exertion of pressure by the pusher on a first fluid supply assembly including a pressure-responsive container to which force is applied by the pusher to mediate fluid flow into the manifold via the first fluid manifold inlet. Once the first fluid is introduced into the manifold flow passage, a syringe coupled with the manifold may be filled by retracting a plunger from a fully forward position to a rearward position in the barrel of the syringe, to thereby cause suction to draw second fluid from the vial or other second fluid container into the manifold flow passage through the second fluid manifold inlet. In such manner, the first and second fluids will intermix in the manifold flow passage and be introduced into the interior volume in the barrel of the syringe in a mixed condition. This mode of operation permits complete mixing of first and second fluids to be effected at the point of use, so that the mixed fluid is immediately available as soon as the syringe is uncoupled from the syringe coupling. In dental anesthetic applications, the dental anesthetic may be the second fluid, and the first fluid may comprise a buffering medium, so that buffered anesthetic is delivered as a mixed fluid to the syringe, in a push (buffering medium delivery)/pull (anesthetic delivery) mode of operation.

In specific embodiments, the anesthetic may be lidocaine, articaine, or marcaine, and the buffering medium may be an aqueous solution of sodium bicarbonate or other buffering agent.

Isolation of the buffering medium from the ambient atmosphere is desired in such applications to avoid oxidative degradation of the buffer, and the buffering medium container therefore is preferably of a suitable gas-tight character.

As discussed earlier, the supply container of anesthetic composition may be of any suitable type, and may for example comprise a vial, cartridge, or other container of commercially available character, such as a Hospira® package of lidocaine hydrochloride.

To avoid oxidative degradation of residual buffering medium in the manifold flow passage after the fill operation has been completed, which could adversely affect subsequent syringe fills, the syringe fill system is desirably operated in the previously described "push-pull" mode that avoids the presence of buffering medium residue in the manifold flow passage after completion of the fill operation, using the buffering medium as the first fluid, and anesthetic as the second fluid.

In such operational mode, the manifold is provided with a first fluid supply check valve 86 having a suitable crack pressure for dispensing the buffering medium in a push mode, as previously described, with the second fluid supply check valve 88 having a crack pressure ensuring that it remains closed and does not enable fluid flow from the manifold flow passage into the second fluid container during dispensing of the first fluid.

Subsequent to such push flowing of the buffering medium as the first fluid into the manifold flow passage, the plunger in the syringe coupled to the syringe coupling of the fill system is retracted. Such retractive action causes a pressure differential to be exerted on the second fluid supply check valve 88, so that check valve 88 opens to allow flow of second fluid from the second fluid container into the manifold flow passage, and through such passage into the syringe, together with the buffering medium previously injected into the manifold flow passage, as the buffered anesthetic mixture.

In this manner, the buffering medium is purged from the manifold flow passage by the flow of the second fluid (anesthetic composition) through the manifold flow passage, thereby "sweeping out" the flow passage to remove the previously dispensed buffering medium therefrom.

It therefore will be appreciated from the foregoing discussion that the manifold may be equipped with check valves at its inlets that have respective crack pressures that differ in relation to one another, in order to accommodate a given mode of dispensing of respective fluids. For example, in one embodiment of the push-pull mode just described, the crack pressure of a check valve in the buffering medium flow path (check valve 86 in FIG. 11) may be in a range of from 6 to 20 psi, and the crack pressure of a check valve in the anesthetic composition flow path (check valve 88 in FIG. 11) may be in a range of from 0.5 to 10 psi, subject to the constraint that the crack pressure of the buffering medium check valve is greater than the crack pressure of the anesthetic composition check valve.

Although the syringe fill system shown in FIGS. 1-11 embodies an arrangement involving "push" of a first fluid and "pull" of a second fluid, it will be appreciated that other arrangements of the syringe fill system of the present disclosure may be employed, in which each of the fluids is dispensed to the syringe in a "push" mode, or in which each of the fluids is dispensed to the syringe in a "pull" mode, or in which a first fluid is dispensed in a "pull" mode and a second fluid is dispensed in a "push" mode, by appropriate provision of valves associated with the respective inlets of the manifold, and arrangement of the respective fluid source containers of the fluids to be mixed with one another for delivery of a mixed fluid to the syringe to be filled.

For example, the respective valves at the inlets of the manifold may be check valves having differing crack pressures, or such valves may be of other suitable types, manual or automatic, that can be selectively actuated for dispensing of a specific fluid from its corresponding supply container, into the manifold flow passage.

It will be appreciated that the valves may be coupled or otherwise arranged for coordinated action, e.g., by use of three-way valves presenting alternative selectable flow paths, wherein the valve associated with each inlet of the syringe fill manifold comprises one of the multiple paths of the valve assembly.

Further, while the syringe fill system has been illustratively shown as employing two fluid source containers for dispensing of fluid to the syringe in the fill operation, it will be appreciated that the manifold may utilize only a single fluid source container in some embodiments, and alternatively may utilize more than two fluid source containers in other embodiments, depending on the specific makeup and character of the composition that is to be provided to the syringe being filled.

The syringe fill apparatus of the present disclosure therefore is advantageously utilized for dispensing of fluid packaged in a fluid container in which downwardly exerted compressive action of the pusher on the container causes fluid to be injected from such container into the manifold, in connection with the manual actuation of the rotary knob to effect rotation of the drive shaft and lead screw so that the pusher travels downwardly on the pusher rail for a predetermined distance corresponding to the pawl engagement of the rotary knob. In this arrangement, the vertically extended dispensing assembly for "push" dispensing is coupled with the pusher whose flange bearing member overlies, i.e., is positioned above, the first fluid supply assembly, so that the dispensing assembly and first fluid supply assembly are arranged in side-by-side relationship to one another, to keep any air atop of the fluid within the fluid containers and out of the manifold flow passage and to provide a remarkably compact (low profile) apparatus conformation to be achieved by the syringe fill system. The horizontally oriented slidable pawl member, with its pawl arm and cogwheel integrated with the rotary knob of the apparatus, further contributes to a low-profile conformation of the apparatus.

It will be recognized that the specific dispensing assembly components may be varied in structure and arrangement, with the dispensing of fluid from the first fluid supply assembly container being carried out in an efficient and accurate manner. It will be further recognized that the dispensing assembly in lieu of manual operation may be adapted for automatic (powered) operation, in any suitable manner.

It will also be appreciated that the syringe fill apparatus may be commercialized or otherwise provided as a fully assembled product comprising the housing and the cassette assembly, and that the cassette assembly may be constituted as a disposable component, and separately resupplied as a replacement cassette assembly article. Alternatively, the cassette assembly article may be packaged and commercialized as a kit with a supply of syringes for use with the syringe fill apparatus when the cassette assembly article is deployed. As a further variation, the fluid source containers for the first and second fluids to be mixed by the syringe fill apparatus may be separately supplied, or alternatively supplied with a cassette assembly, with or without syringes for use therewith. As a further variation, the fluid source containers for the first and second fluids to be mixed by the syringe fill apparatus may be separately supplied, or alternatively supplied with syringes, with or without a cassette for use therewith. The present disclosure contemplates all permutations of such constituent components as potential parts of a kit supplied to an end user utilizing the syringe fill system to load syringes and use same. Kits containing components of the syringe fill system may include appropriate printed instructions for use of the system and/or the kit.

As a still further variation, syringes rather than being supplied an empty condition for filling by the syringe fill apparatus, may be partially prefilled, and supplied for use with the syringe fill apparatus to mix the pre-filled fluid in the syringe with additional fluid dispensed from the syringe fill apparatus. For example, syringes may be provided with a partial fill of solid buffering agent that then is solubilized in fluid subsequently introduced to the syringe in the syringe fill operation. Alternatively, other solid form materials could be prefilled in syringes that are subsequently filled with fluid using the syringe fill system of the disclosure.

The syringes that are filled with the syringe fill apparatus of the present disclosure can be of any suitable type.

Figure 12:
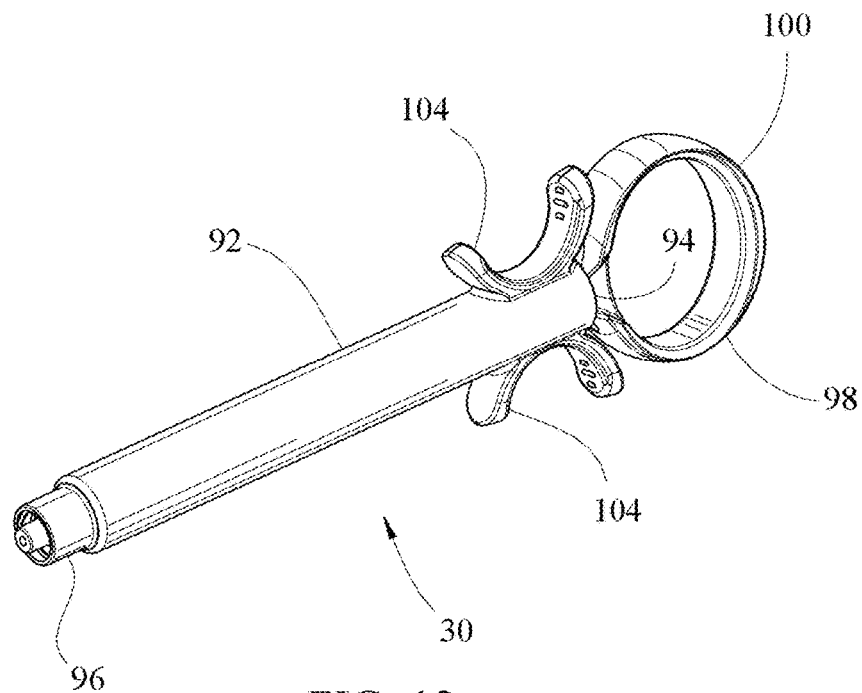
FIG. 12 is a perspective view of a syringe according to one embodiment of the present disclosure.

FIG. 12 is a perspective view of a syringe according to one embodiment of the present disclosure. The syringe 30 includes a barrel 92, open at its proximal end 94, and including a luer lock distal end portion 96 for attachment to a syringe coupling of a syringe fill system, an injection needle, or coupling with a fluid flow circuit. The distal end portion thus may be differently configured, with different engagement or coupling structure.

The barrel 92 of the syringe encloses a cylindrical interior volume in which is disposed a plunger 98 for slidable translation therein. The plunger 98 includes thumb ring 100 at its proximal end, with a plunger stem 102, as described more fully hereinafter. The barrel on its upper exterior surface has finger grips 104 secured thereto, being integrally formed with the barrel or otherwise secured thereto.

Figure 13:
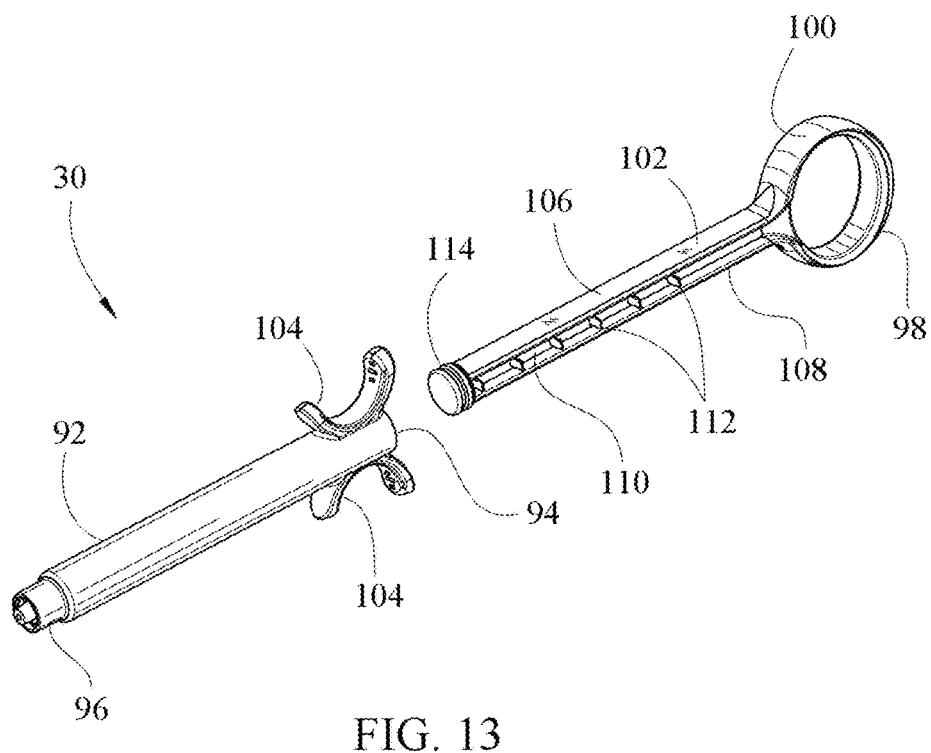
FIG. 13 is an exploded view of the syringe of FIG. 12.

FIG. 13 is an exploded view of the syringe 30 of FIG. 12, wherein previously described parts and features are correspondingly numbered with respect to FIG. 12. As shown, the plunger 98 includes a proximal thumb ring 100 which is connected to a central plunger spine 110 joined in turn to a top side rail 106 and a bottom side rail 108, with lateral fingers 112 extending outwardly from the plunger spine at regular spaced-apart intervals, along a longitudinal extent of the plunger spine. A stopper element 114 is mounted at the distal end of the plunger stem.

Figure 14:
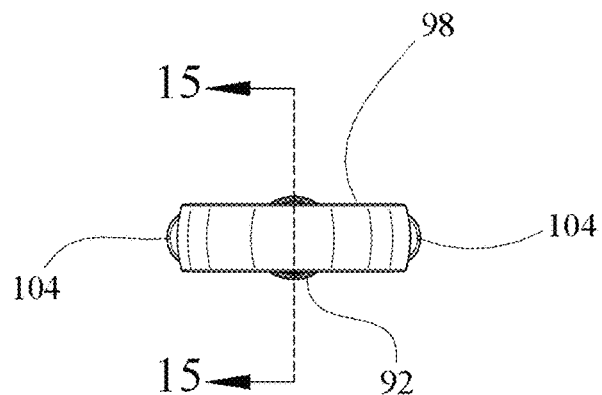
FIG. 14 is a top plan view of the syringe of FIGS. 12 and 13.

FIG. 14 is a top plan view of the syringe of FIGS. 12 and 13.

Figure 15:
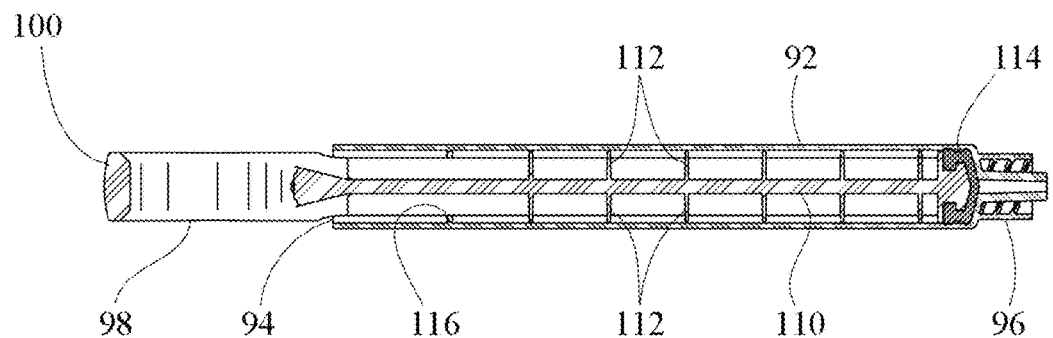
FIG. 15 is a sectional longitudinal view of the syringe of FIGS. 12-14.

FIG. 15 is a sectional longitudinal view of the syringe of FIGS. 12-14, wherein corresponding features and elements are correspondingly numbered with respect to FIGS. 12-14. As shown, the barrel is formed with an inwardly extending protrusion 116 that is circumferentially continuous at an interior proximal portion of the barrel. The outwardly extending lateral fingers 112 are longitudinally spaced apart from one another in series, so that their spacing dimension defines a single dose of the fluid to be administered, by forwardly translating the plunger in the barrel toward the distal end; similarly, the spacing corresponds to single doses of the fluid to be drawn into the syringe for subsequent administration.

The purpose of the construction shown in FIGS. 12-15 is to provide a syringe with audible and haptic feedback character. With the plunger fully retracted and the syringe in a loaded state, the forward motion of the plunger will cause the lateral fingers 112 to successively encounter the inwardly extending protrusion 116. The syringe user will then feel the resistance of the finger against the protrusion, and thereby know that a unit dose can be administered by forwardly pushing the plunger 98 in the barrel 92.

As the finger passes the protrusion, it is rearwardly deformed and then released from the protrusion, with such frictional engagement and subsequent disengagement producing a haptic response and audible signal to the syringe user communicating that administration of a unit dose of the fluid has been initiated. Continued forward translation of the plunger then will advance the plunger to the point that the next successive lateral finger 112 will come into contact with the protrusion, and the corresponding resistance will be sensed by the syringe user as indicating that a unit dose administration of fluid has been completed.

The user then has the option of administering a second unit dose of the fluid by advancing the plunger past the protrusion, providing an audible signal that the administration of the second unit dose has been initiated, with further advancement of the plunger bringing the protrusion into contact with the next succeeding lateral finger, with the corresponding resistance indicating to the syringe user that the completion of administration of the second unit dose has been achieved.

Alternatively, the syringe user after the administration of the first unit dose of fluid may withdraw the syringe from the locus at which the first dose has been administered, and position the syringe for administration at a second locus for administration of a unit dose at the second location.

In this manner, the syringe provides auditory and haptic feedback, to enable the syringe user to achieve precisely metered administration of unit doses of fluid. Such auditory and haptic feedback thereby enables precision injection of fluid to achieve the desired therapeutic or other outcome, without the need for visual confirmation of dose volume. In applications such as the administration of dental anesthetic, where visual confirmation inside a patient's mouth is difficult, such precise dose administration avoids the unwanted occurrences of administering inadequate analgesia or alternatively of over-anesthetizing a patient in a specific locus, beyond what is necessary for the therapeutic intervention.

As mentioned, the lateral fingers on the spine of the plunger in the syringe of the present disclosure are deformable in engagement with, and in release from, the circumscribing protrusion on the interior surface of the syringe barrel. For such purpose, the lateral fingers are suitably formed of a deformable resilient material that will deform while passing the circumscribing protrusion in the syringe barrel, with an appropriate audible character when passing and releasing from the protrusion, e.g., a snap or clicking sound, and that will resiliently regain its orientation upon release from the protrusion.

It will be appreciated that the lateral fingers can be formed of any of a variety of materials, e.g., polycarbonate, polypropylene, polyethylene, hard rubber, polyurethane, or other suitable material(s) of construction. Such lateral fingers can be integrally molded with the spine and rails of the plunger, or alternatively can be press-fit in receiving grooves in the spine, mechanically secured, or otherwise affixed to the plunger spine. In like manner, the circumscribing protrusion on the interior surface of the syringe barrel may be formed of any suitable material, including those identified above as materials of construction of the lateral fingers. The specific dimensions of the circumscribing protrusion will be selected so that the interaction of the lateral fingers with the protrusion produces the desired audible signal and kinesthetic feedback to the syringe user. Suitable dimensions can be readily empirically determined for specific materials of construction, without undue experimentation, based on the disclosure herein.

It will be recognized that syringes may be employed utilizing a wide variety of audible and haptic feedback structures and arrangements, to facilitate a precise administration of injected fluid.

The haptic feedback and audible output syringes of the present disclosure may be provided in a kit comprising a multiplicity of syringes, in which the syringes comprise one or more syringes of the present disclosure. Such kit may comprise material to be administered by the syringes, e.g., anesthetic and/or buffering agent.

The disclosure contemplates a method of administering fluid to a subject in a therapeutic intervention, in which the method comprises at least partially filling a syringe of the present disclosure with a therapeutic fluid, and administering the therapeutic fluid to the subject from the syringe in a manner generating haptic feedback and audible output indicative of administered dose of the therapeutic fluid.

It will be recognized that the syringe fill systems and subassemblies of the present disclosure may be widely modified and varied in practice to accommodate a wide variety of component fluids and therapeutic material, and to provide additional monitoring and control capability in the syringe fill operation.

For example, the syringe fill system may comprise indicator lights, such as LEDs of differing colors, to indicate an operational state or condition of the syringe fill system. The syringe fill system may in other implementations comprise gauges, monitors, and other output features to provide a user with relevant information for the syringe fill process, e.g., information concerning temperatures of fluid in the source containers, degree of completion of the syringe loading operation, cumulative number of syringe loading operations performed in a specified time period, etc.

The syringe fill system may also be provided with data communication and/or signal processing capability, e.g., a port for connection to a data communication or processing network, wireless connectivity to a fluid inventory monitoring system, etc. The syringe loading system may also be equipped with various input features and capability, such as settings mechanisms to accommodate syringes of varying sizes, types of fluids, etc.

The syringe fill system may additionally, or alternatively, be constructed to incorporate in the interior volume of the housing or otherwise in association with fluid supply containers a heat source, such as an electrical resistance heating element, or other heater component, serving to maintain the fluids in the respective source containers at temperature appropriate for physiological administration.

Although the syringe fill system of the disclosure is illustratively shown herein as being adapted for single syringe filling at a given time, it will be appreciated that the syringe fill system in other embodiments may be constructed to simultaneously fill multiple syringes with fluids for use. The syringe fill system may therefore be equipped with a magazine, carousel, or other feed mechanism for coupling multiple syringes with respective fill manifolds or different flow circuits connected to a single unitary fill manifold, so that all such coupled syringes are loaded for use, e.g., as a centralized syringe loading system accommodating a number of concurrent users, or as a system in which all such coupled syringes are simultaneously filled for use, as may be advantageous when a series of injections with disposable syringes are required for a given therapeutic procedure.

The syringe fill system of the present disclosure in other embodiments comprises:
a syringe fill manifold including a manifold fill passage, an inlet for connection to a fluid supply assembly, and an outlet arranged to deliver fluid for syringe filling;
a fluid supply assembly adapted to receive a fluid container so that the fluid container is positioned above the syringe fill manifold and is coupled to the inlet of the syringe fill manifold, with a valve, e.g., a one-way valve, at the inlet to control flow of fluid from the fluid container to the manifold fill passage; and a dispensing assembly including a dispensing selector member operatively linked to an actuator member arranged to control dispensing of fluid from the fluid container in an amount selectable by the dispensing selector member, wherein the fluid supply assembly and the dispensing assembly are arranged in side-by-side relationship with one another.

In such other embodiments of the syringe fill system, as hereinafter more fully described, the dispensing selector member in the dispensing assembly is operatively linked via compression and torsional springs with the actuator member, and the actuator member is arranged for downward, e.g., vertical downward, travel on a lead screw in response to rotational movement of the dispensing selector member followed by downward translation of the dispensing selector member, with the actuator member during downward translation on the lead screw causing fluid to flow from the fluid container to the manifold fill passage of the syringe fill manifold, and with the compression spring acting to return the dispensing selector member to a starting position after the amount of fluid selected by the dispensing selector member has been flowed from the fluid container to the manifold fill passage of the syringe fill manifold.

In this syringe fill system, the dispensing selector member can be fabricated and arranged so that it is translatable to cause display of a corresponding selected amount of fluid.

The syringe fill system described above, apart from the arrangement including the dispensing assembly operatively linked via compression and torsional springs with the actuator member, may be constituted in a manner similar to the syringe fill system of embodiments described elsewhere herein.

Figure 16:
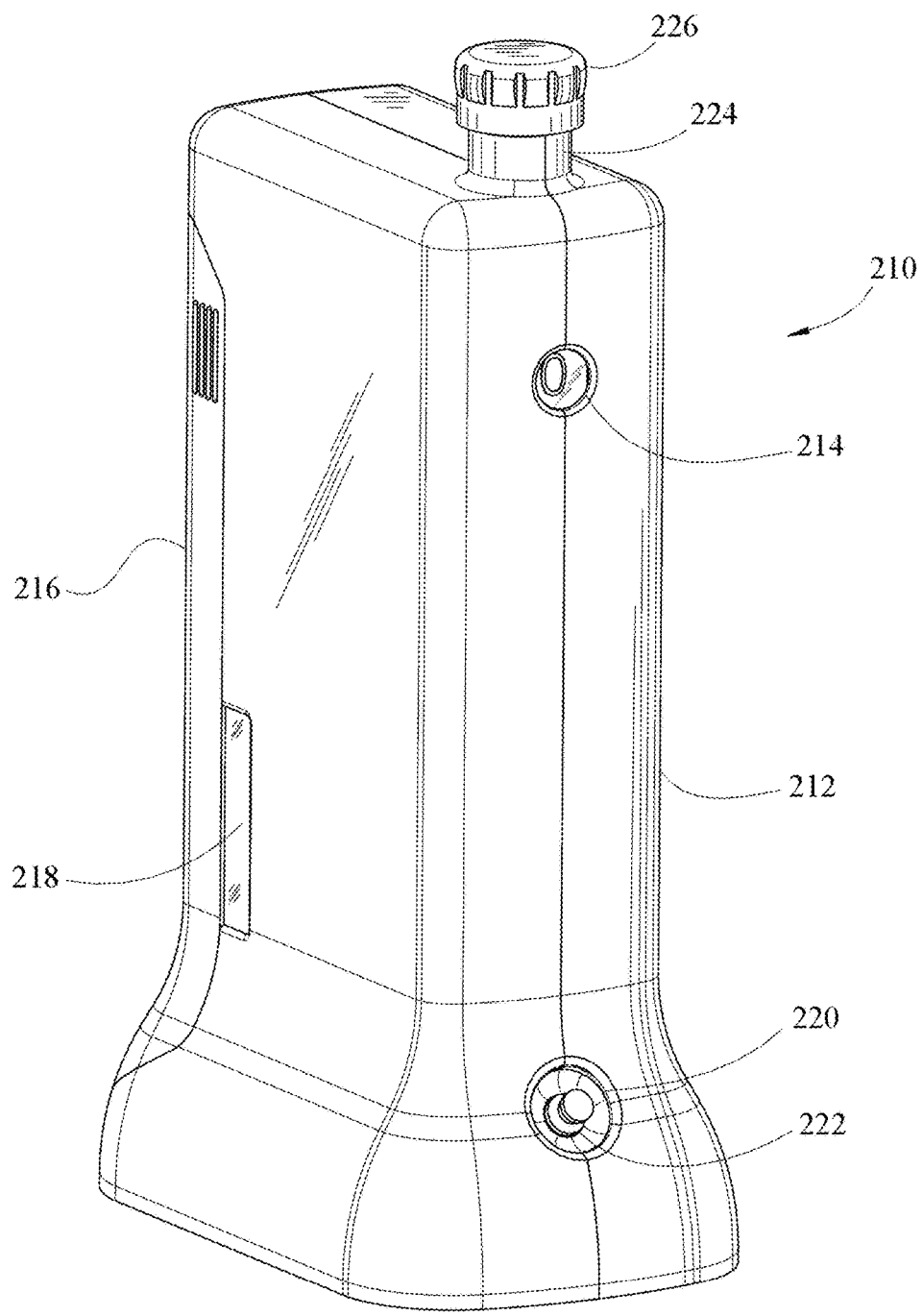
FIG. 16 is a perspective view of a syringe fill system, according to one embodiment of the disclosure.

Referring to the drawings, FIG. 16 is a perspective view of a syringe fill system 210 according to one embodiment of the disclosure. The fill system 210 includes housing 212. On the upper front face of the housing is a viewing port 214 for viewing the dispensing setting of the system, as described hereinafter in greater detail. The front face of the housing at its lower portion includes a syringe coupling port 220 presenting syringe coupling 222.

At its rear portion, the housing 212 includes a removable section 216, permitting access to internal components in the interior volume of the housing. The rear portion of the housing also includes a viewing window 218, permitting visual verification of fluid inventory in a fluid dispensing container in the housing interior volume. At its upper portion, the housing includes a cylindrical sleeve 224 from which upwardly extends a dispensing selector knob 226, the function of which is described hereafter.

Figure 17:
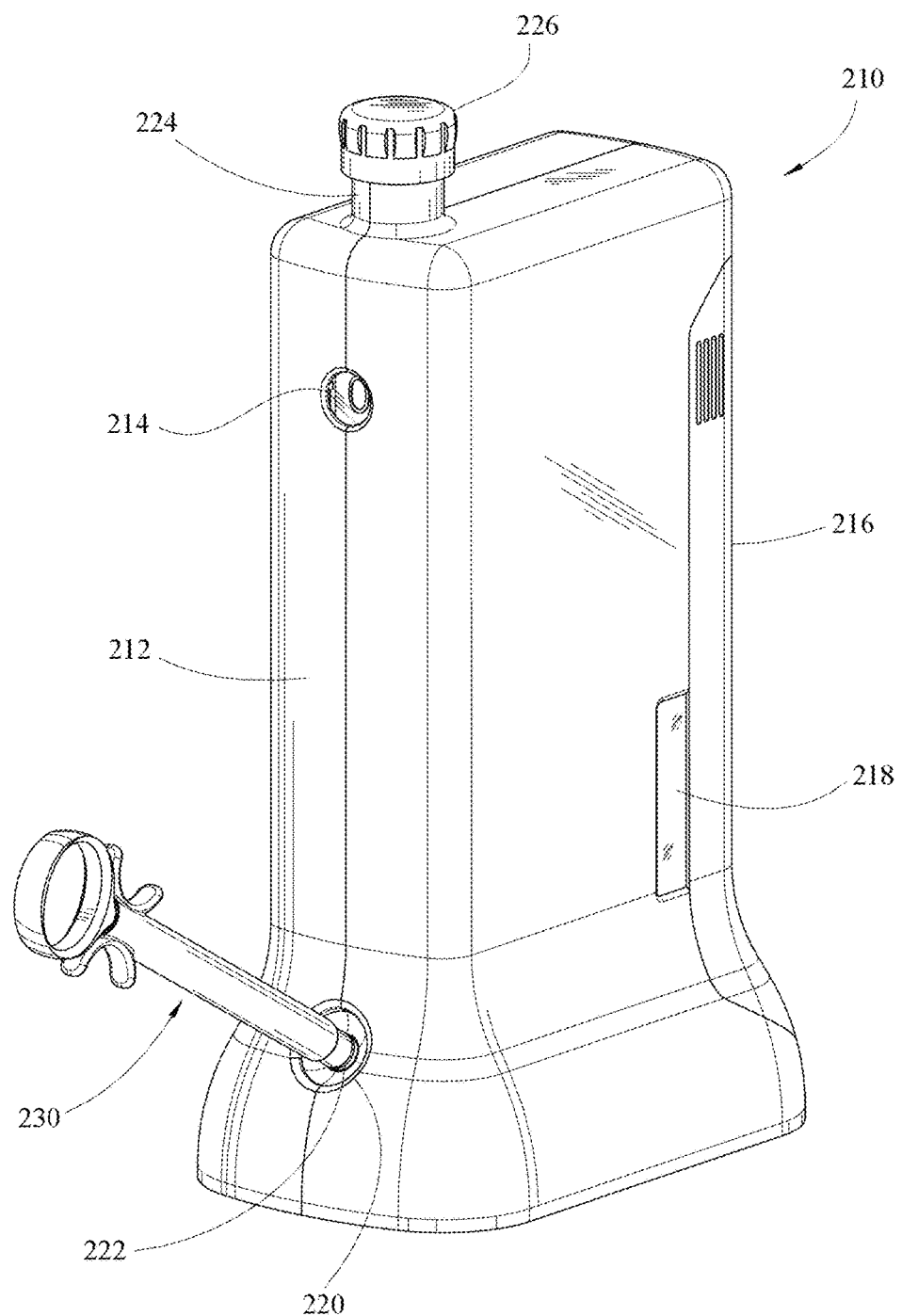
FIG. 17 is a perspective view of the syringe fill system of FIG. 16, with a syringe engaged for filling.

FIG. 17 is a perspective view of the syringe fill system 210 of FIG. 16, showing a syringe 230 engaged with the syringe coupling 222 in syringe coupling port 220.

Figure 18:
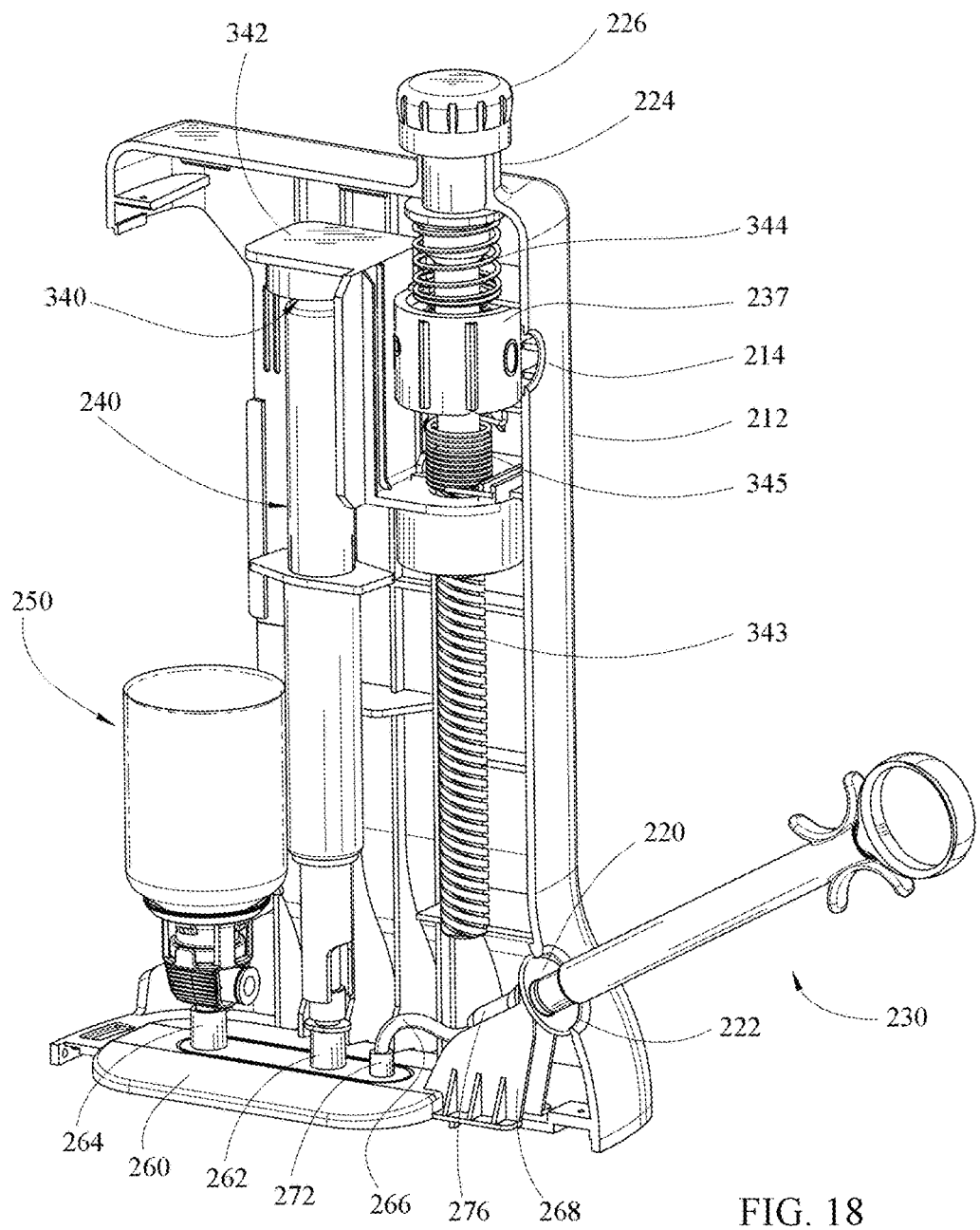
FIG. 18 is a partial breakaway perspective view of a portion of the syringe fill system of FIGS. 16 and 17.
Figure 19:
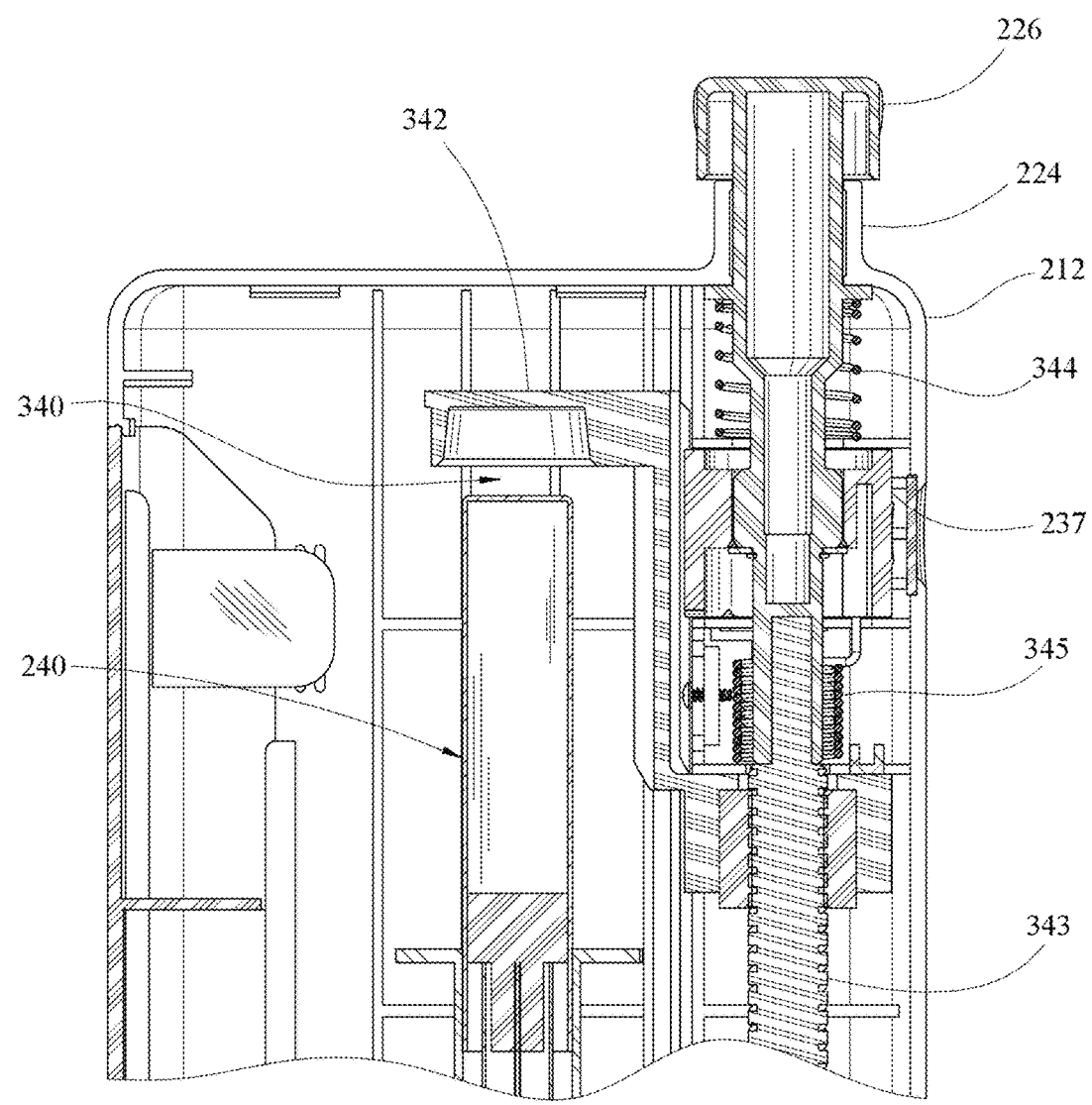
FIG. 19 is a cross-sectional elevation view of a portion of the syringe fill system of FIGS. 16-18, showing the details of the components thereof.

FIG. 18 is a partial breakaway view of the syringe fill system of FIGS. 16 and 17, showing the details of the components contained in the housing 212. FIG. 19 is an enlarged sectional elevation view of a portion of the syringe fill system, showing the details of the dispensing assembly and first fluid supply assembly thereof.

As illustrated in FIGS. 18 and 19, the dispensing selector knob 226 mounted in cylindrical sleeve 224 of the housing 212 is secured to a lead screw 343 and coupled with an actuator 342, in an assembly including compression spring 344, indicator ring 237, and torsion spring 345. In the view illustrated, the actuator 342 is positioned with a gap 340 between it and the first fluid supply assembly 240. The first fluid supply assembly 240 in turn is coupled at its lower end to inlet 262 of the manifold 260.

The system as shown in FIG. 18 further includes a second fluid supply assembly 250. The second fluid supply assembly 250 is coupled at its lower end to inlet 264 of the manifold 260. The manifold 260 includes fluid outlet 272, to which is joined the discharge line 266. The discharge line 266 in turn is connected in fluid flow relationship with syringe adapter 276 mounted on syringe engagement support 268. The syringe adapter 276 includes syringe coupling 222 positioned in the syringe coupling port 220, as previously described.

In operation of the FIGS. 16-19 syringe fill system, a user rotates selector knob 226 to select an amount of fluid to be dispensed from the first fluid supply assembly 240. For this purpose, the indicator ring 237 may be marked at intervals around the circumference with numbers corresponding to the number of doses of fluid that will be dispensed by the system to the syringe 230 when a specific dosage number is selected so that it is visible in the viewing port 214.

The gap 340 exists to allow the user stroke of the selector knob 226 to be significant and appropriate in character, and to allow downward translation of activating member 342 from lead screw rotation, coupled to selector knob 226 rotation, so that the actuator 342 engages the first fluid supply assembly 240 without premature injection of its fluid contents into the manifold 260.

The user then pushes down dispensing selector knob 226, so that the actuator 342 engages the first fluid supply assembly to inject fluid from the first fluid supply container in such assembly, into the manifold.

Upon release of the dispensing selector knob 226, the compression spring returns the dispensing selector knob to an upper position, torsion spring 345 rotates the indicator ring 237 to a "zero" position and the gap 340 is reset to an original, preset distance. The actuator then is in a new corresponding lowered position, having translated down lead screw 343 as the fluid container in the first fluid supply assembly expelled fluid to the manifold.

By this arrangement, the first fluid supply assembly 240 utilizes a fluid container in which the downwardly exerted compressive action of the actuator 342 on the container causes fluid to be injected from such container into the manifold. The container may be of any suitable type that is adapted to such fluid injection operation, in which fluid is pushed (by compressive force) into the manifold. In this "push" configuration, the dispensing assembly, including the dispensing selector knob 226, compression spring 344, indicator ring 237, torsion spring 345, and lead screw 343, is arranged in side-by-side relationship to the first fluid supply assembly 240.

By this arrangement, in which the vertically extended dispensing assembly is interconnected via the actuator 342 with the vertically extended first fluid supply assembly, the side-by-side relationship of the dispensing assembly and fluid supply assembly enables a remarkably compact (low profile) apparatus conformation to be achieved in the syringe fill system.

It will be recognized that the specific dispensing assembly components may be varied in structure and arrangement, so that the dispensing of fluid from the first fluid supply assembly container is carried out in an efficient and accurate manner. It will be further recognized that the dispensing assembly in lieu of manual operation may be adapted for automatic (powered) operation, in any suitable manner.

Figure 20:
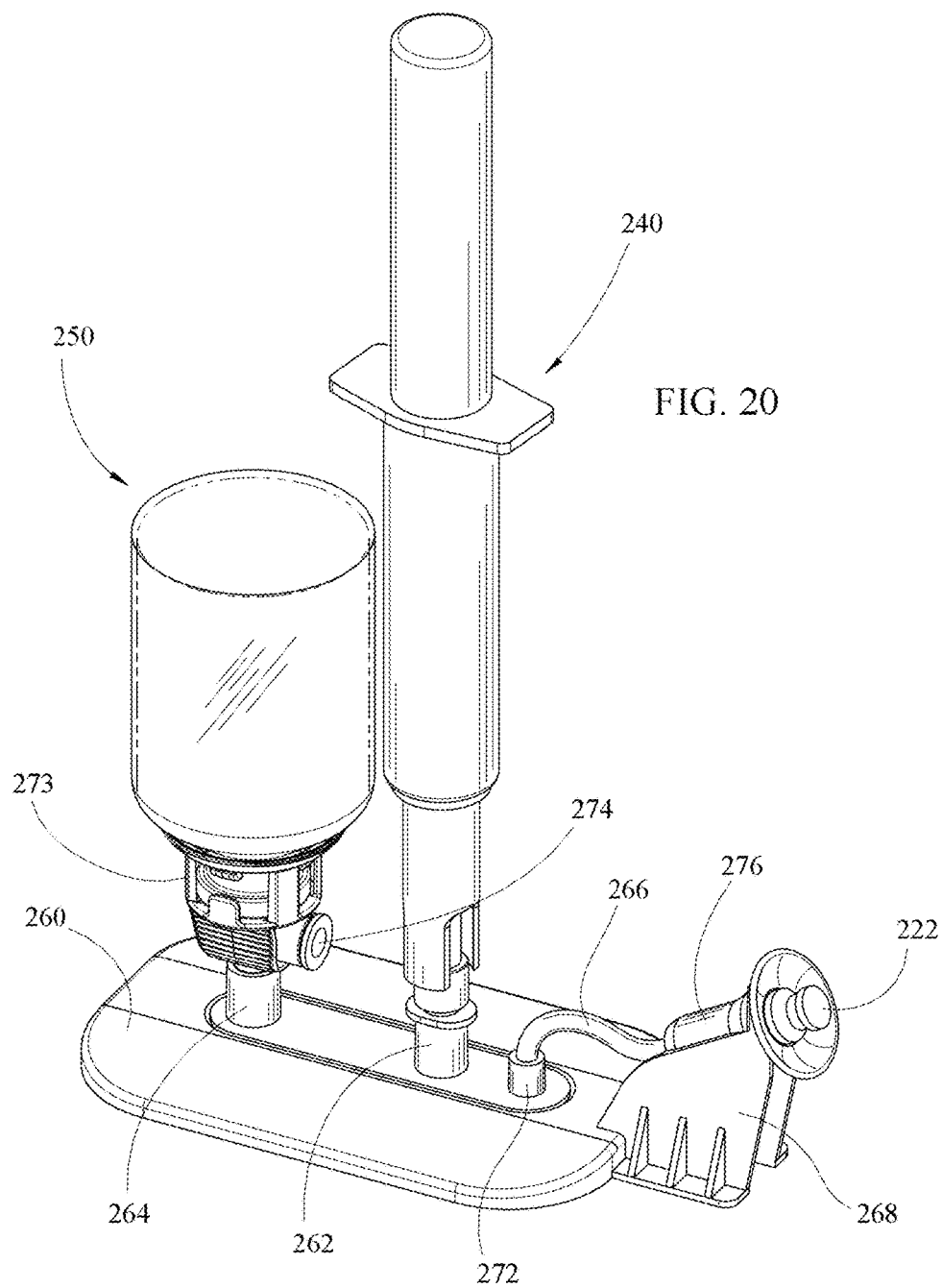
FIG. 20 is a perspective view of a syringe fill system subassembly of the FIGS. 16-19 syringe fill system.
Figure 21:
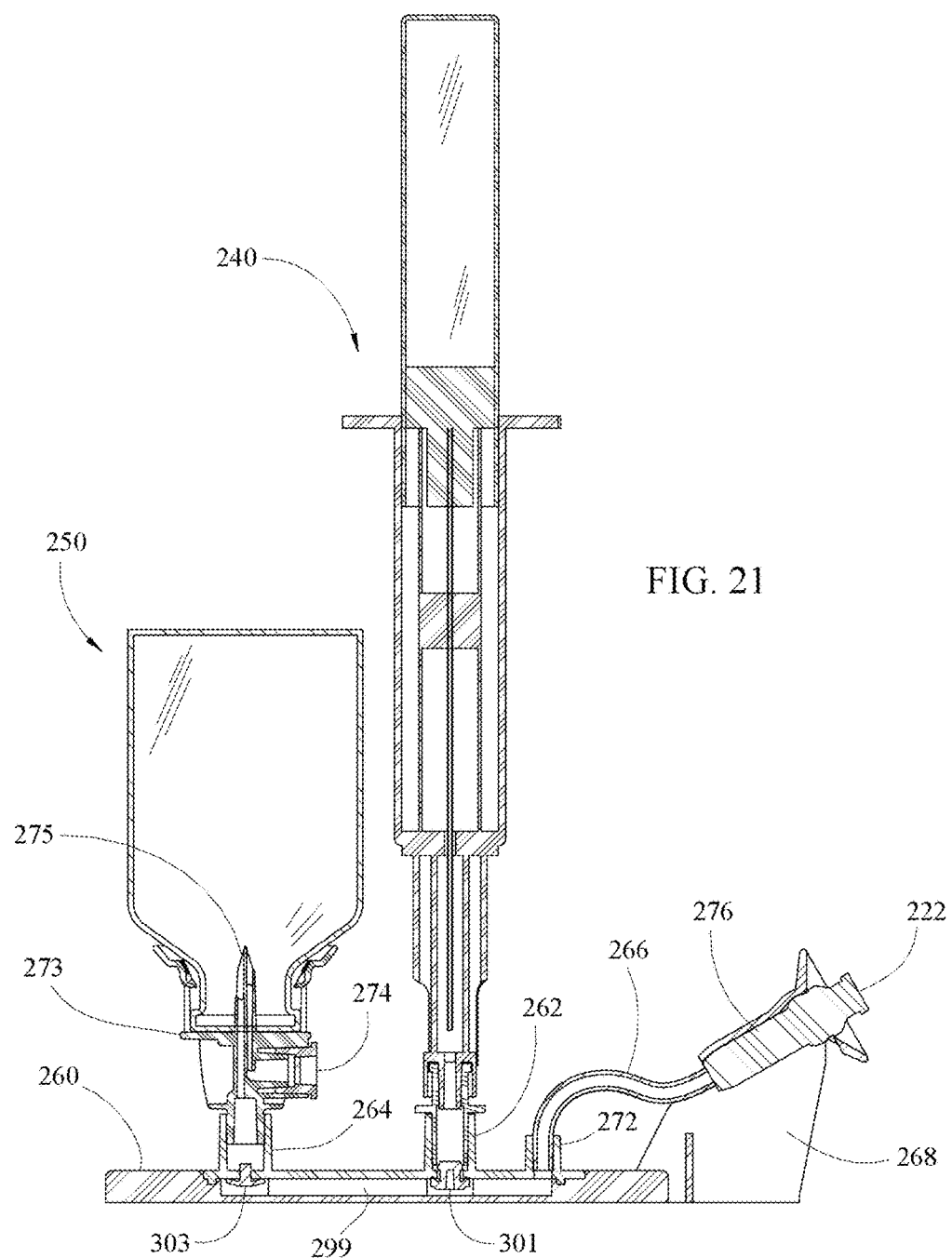
FIG. 21 is a cross-sectional elevation view of the syringe fill system subassembly of FIG. 20.

FIG. 20 is a perspective view of a subassembly of the FIGS. 16-19 syringe fill system, and FIG. 21 is a cross-sectional elevation view thereof, showing the details of construction of such subassembly.

As illustrated in FIGS. 20 and 21, the subassembly includes manifold 260 having syringe engagement support 268 secured thereto. The manifold 260 defines a manifold flow passage 299 as shown in FIG. 21, and includes first fluid supply inlet 262 having first fluid supply assembly 240 coupled thereto, second fluid supply inlet 264 having second fluid supply assembly 250 coupled thereto, and fluid outlet 272. In the respective first and second fluid supply inlets 262 and 264 are disposed check valves (e.g., one-way valves) 301 and 303, respectively, to control flow of fluid into the manifold flow passage 299 from the first fluid supply assembly 240 and second fluid supply assembly 250, respectively.

The second fluid supply assembly 250 as illustrated includes a second fluid supply assembly container sleeve 273, for receiving a container of second fluid. The second fluid supply assembly 250 includes a spike 275 for piercing a cap or cover of the second fluid supply container when received in the sleeve 273, and an air inletting vent 274 enabling air to enter the container to facilitate dispensing of fluid from the second fluid supply container. The air inletting vent 274 may comprise a suitable filter effective to remove airborne contaminants that might otherwise adversely affect the second fluid. For example, a 0.2 µm hydrophobic filter may be employed to maintain fluid in the second fluid supply container in a sterile condition, while enabling efficient dispensing of fluid from such container to be carried out.

The manifold fluid outlet 272 is coupled with a discharge line 266 that communicates with the syringe adapter 276 terminating in syringe coupling 222. The syringe adapter 276 is mounted on syringe engagement support 268, and the syringe adapter may be oriented on such support at any suitable angle desired for coupling with a syringe to be filled by the syringe fill system.

The subassembly shown in FIGS. 20 and 21 is adapted to be installed in the housing illustrated in FIGS. 16-19, and can be supplied as a unitary subassembly, e.g., as a disposable unit that may be utilized for fluid filling of syringes from a set of first and second fluid containers, and then discarded for recycling or other disposition.

The subassembly may be adapted to be packaged and sold as a disposable unit, e.g., wherein the syringe fill system subassembly is fabricated predominantly (such as greater than 50% by weight of the subassembly) of biodegradable plastic and elastomeric material(s) of construction, or otherwise configured as a disposable or single-use product.

The second fluid supply assembly in the FIGS. 16-21 system can be utilized for dispensing of a second fluid from a second fluid container in a "draw" or "pull" mode, in which a syringe is coupled with the syringe coupling 222 of the syringe adapter 276, and the plunger of the syringe is retracted to flow the second fluid from the second fluid container through second fluid supply inlet 264, into and through the manifold flow passage 299 to the syringe. For such purpose, the second fluid supply check valve 303 should have a "crack pressure"—i.e., the pressure at which the check valve will open to accommodate flow therethrough—that accommodates such pull mode of syringe filling.

In various applications, it may be desired to operate the syringe fill system of the type illustrated in FIGS. 16-21 so that one of the fluid supply check valves 301 and 303 is closed while the other one of such valves is open, and the respective valves for such purpose may have different crack pressure ratings to accommodate the desired dispensing operation.

Although the syringe fill system shown in FIGS. 16-21 embody an arrangement involving "push" of a first fluid and "pull" of a second fluid, it will be appreciated that other arrangements of the syringe fill system of the present disclosure may be employed, in which each of the fluids is dispensed to the syringe in a "push" mode, or in which each of the fluids is dispensed to the syringe in a "pull" mode, or in which a first fluid is dispensed in a "pull" mode and a second fluid is dispensed in a "push" mode, by appropriate provision of valves associated with the respective inlets of the manifold.

For example, the respective valves at the inlets of the manifold may be check valves having differing crack pressures, or such valves may be of other suitable types, manual or automatic, that can be selectively actuated for dispensing of a specific fluid from its corresponding supply container, into the manifold flow passage.

It will be appreciated that the valves may be coupled or otherwise arranged for coordinated action, e.g., by use of three-way valves presenting alternative selectable flow paths, wherein the valve associated with each inlet of the syringe fill manifold comprises one of the multiple paths of the valve assembly.

Further, while the syringe fill system has been illustratively shown as employing two fluid supply assemblies for dispensing of fluid to the syringe in the fill operation, it will be appreciated that the manifold may utilize only a single fluid supply assembly in some embodiments, and alternatively may utilize more than two fluid supply assemblies in other embodiments, depending on the specific makeup and character of the composition that is to be provided to the syringe being filled.

FIG. 22 is a perspective view of another syringe that may be employed with the syringe fill system of the present disclosure. The syringe 230 includes a syringe barrel 282 enclosing an interior volume of the syringe. The syringe barrel 282 terminates at a distal end portion 284. The syringe barrel 282 includes an open proximal end 286 at the proximal end portion 288 of the syringe barrel.

Disposed in longitudinally slidable relationship in the interior volume of the syringe is a plunger 298 at the distal end of a plunger member stem 302. The plunger member stem 302 is formed at its proximal end with thumb ring 304. At the proximal end portion 288 of the syringe barrel are disposed finger grips 290. The finger grips 290 are integrally joined at their medial portions 292 to the exterior surface of the syringe barrel. Each of the finger grips includes arcuate segments 294, 296. The finger grips alternatively may be of a closed ring character.

The syringe depicted in FIG. 22 incorporates a kinesthetic feedback feature, with coaction members on each of the plunger member stem and syringe barrel interior surface that interact with one another during translation of the plunger in the interior volume of the syringe barrel. The coaction members 247, 249, 251, and 253 are at longitudinally spaced-apart at intervals along the length of the syringe, corresponding to fluid volumes for successive doses of administered therapeutic agent.

The coaction members are shown in the enlarged cross-sectional elevation view of a portion of the FIG. 22 syringe 230, in FIG. 23. As illustrated, the coaction members 247 include inwardly extending protrusion 257 on the inner surface of syringe barrel 282 and outwardly extending protrusions 259 on the plunger member stem 302. As the plunger member stem is translated in the interior volume of the syringe barrel, the outwardly extending protrusion on the plunger member stem will encounter the inwardly extending protrusion on the syringe barrel inner surface, and the "bump" or "click" that results from the contact of such protrusion members will be sensed by the syringe user.

Thus, the user may sense such kinesthetic feedback from interaction of the coaction members, and initiate an injection, stopping the injection upon sensing resistance of a subsequent protrusion element. For a subsequent injection, the plunger member is distally advanced in the barrel until resistance is sensed of a next-succeeding protrusion element, and so on. In this manner, the syringe provides sensory feedback to the user, to enable administration of a precise bolus of fluid.

It will be recognized that syringes may be employed utilizing a wide variety of kinesthetic feedback structures and arrangements, to provide a precise administration of injected fluid.

Syringes of the type shown in FIGS. 22 and 23 may be provided as components of kits including other components of the syringe fill system, as previously described.

The disclosure in a further aspect relates to a syringe fill device for filling a syringe with a composition, comprising:
a fill station housing defining an interior volume therewithin;
a feed manifold mountable in the interior volume, such feed manifold including (i) passageways with inlets that are adapted to engage fluid carpules when mounted in the interior volume in flow communication with said inlets, and (ii) a syringe engagement port communicating with the passageways, and configured to mate with a distal end of a syringe body so that fluid flowing through the feed manifold flows into the syringe body; and
a drive assembly adapted to be coupled with fluid carpules mountable in the interior volume, and arranged to effect fluid flow from at least one of the fluid carpules through the feed manifold to the syringe engagement port;
the housing being configured to receive the distal portion of a syringe body in the interior volume so that the distal end of the syringe body mates with the syringe engagement port of the feed manifold for filling of the syringe with fluid from one or more carpules mounted in the interior volume of the fill station housing.

The drive assembly in such syringe fill device can be of any suitable type for effecting dispensing of fluid from carpules in the interior volume of the fill station. In various embodiments, the drive assembly applies force to the carpule to hydraulically fill the syringe. The drive assembly may be of automated character, whose operation is enabled by a power supply such as an electrical power line, electrochemical cells, solar cells, etc. Alternatively, the drive assembly may be of a manually operated character, e.g., utilizing manually applied force to exert pressure on the fluid in the fluid carpule in the use of the syringe fill device. In one embodiment, the manually operated drive assembly may include thumb pressure-actuated plungers, where the plunger sealing element is disposed at a proximal end portion of a fluid-filled carpule, so that thumb pressure exerted on the proximal end of the plunger member effects a forward movement of the plunger sealing element, causing fluid to be dispensed from the carpule.

The drive assembly may for example comprise a motor drive assembly, comprising a separate motor coupled with a drive piston, for each fluid carpule mountable in the interior volume, wherein each separate motor and coupled drive piston is independently actuatable when the motor is powered, so that the drive piston is compressively engaged with a corresponding carpule to cause fluid from the carpule to flow through a passageway of the feed manifold to the syringe engagement port.

The syringe engagement port may be configured in any suitable manner to mate with the distal end of a syringe body, to enable filling of the syringe with fluid deriving from the carpule(s) of the syringe fill device. For such purpose, the syringe engagement port may include mounting, fixturing, or coupling structure of any suitable type. In various embodiments, the syringe engagement port comprises a luer lock structure for lockingly engaging the distal end of a syringe body. In various embodiments, the syringe fill device comprises an arrangement for maintaining sterile conditions at the syringe engagement port, such as UV lighting from a UV light source arranged to impinge UV radiation on the syringe engagement port, and optionally on other regions in, on or in proximity to the syringe fill device.

The syringe fill device of the present disclosure is preferably adapted to minimize mixing of different fluids outside of the interior volume of the syringe being filled. Accordingly, the syringe fill device may be configured and adapted to segregate flows of the respective fluids upstream of the syringe, to minimize mixing of the respective fluids prior to their introduction into the interior volume of the syringe.

The fill station housing may be of any suitable shape, and may for example comprise a generally cylindrical or other shaped housing that is mounted on a suitable base or support structure. The housing may be formed with a slidable or hinged door allowing access to the interior volume of the housing, for installation therein or servicing of components disposed in the interior volume. For example, the housing may be fabricated with a removable tray structure on which the fluid carpules can be mounted, and the tray structure may also be adapted for engagement with the feed manifold of the syringe fill device, e.g., so that the fluid carpules are snapped into place with their distal (discharge) end portions engaged with the feed manifold on the tray structure.

The carpules themselves may be of any suitable form, and may for example comprise cylindrical fluid packages, in which the package has a distal discharge nozzle adapted for coupling with an inlet end of the feed manifold. At its proximal end portion, the cylindrical fluid package may contain a stopper that is axially translatable in the interior volume of the cylindrical package, to enclose a fluid volume in the carpule interior volume. The stopper can be engaged with and translated forwardly toward the distal end of the carpule package, to cause fluid to be dispensed from such distal end.

The syringe fill device may be constructed and arranged to hold any number of carpules of fluid for filling of syringes. While the syringe fill device is illustratively described herein as containing two carpules, it will be recognized that the syringe fill device in some embodiments may contain only a single carpule, and in others may contain three, four, or more carpules. In still other embodiments, a magazine containing a plurality of carpules may be employed, or a rotatable carousel may be arranged to be selectively positioned, with a particular one or ones of the multiple carpules on the carousel being engageable with the feed manifold. For such purpose, the feed manifold may be provided with a corresponding number of flow passages and inlets for coupling of the feed manifold with the carpules to be employed in the dispensing operation, for syringe filling.

As is apparent from the foregoing discussion, the carpules in the syringe fill device may contain components of a multicomponent therapeutic composition that is intended to be subsequently delivered by syringe administration to a patient, or the carpules may alternatively contain single component fluids or single agent solutions. It will be recognized that the syringe fill device may be variously configured and arranged to accommodate a wide variety of fluid media for syringe filling.

The feed manifold may be correspondingly varied in form and construction, to provide fluid passage(s) for flow of fluid from carpule(s) to the syringe being filled.

In one advantageous arrangement, the feed manifold comprises an axially elongate leg, and angularly divergent legs. Each of the angularly divergent legs has a proximal end portion adapted for coupling with a distal end portion of a separate fluid carpule, and enclosing a divergent leg fluid flow passage. Each of the angularly divergent legs has a distal end portion coupled to the axially elongate leg. The axially elongate leg encloses two separate flow passages extending along the axially elongate leg, each separate flow passage being coupled to a respective one of the divergent leg fluid flow passages so that flows of fluids from separate carpules coupled to the feed manifold are not intermixed with one another in the axially elongate leg.

In various embodiments, in which the syringe fill device is configured to provide two fluids to a syringe in the fill operation, for mixing of such fluids in the barrel chamber of the syringe, the manifold may be configured with a "Y" shape, or a wishbone shape. In other embodiments, in which the syringe fill device is configured to provide 3, 4 or more fluids to the syringe in the fill operation, the manifold may be configured with a spider conformation, in which flow passage legs, e.g., in the form of tubes are conduits, are provided for coupling with respective carpules at one end thereof, with the other end of such flow passage legs being in fluid flow communication with a main flow passage member, in which respective flows of the different fluids may be separated from one another, e.g., in separate bores, passages, or flow compartments of the main flow passage member, to avoid substantial mixing before the fluids enter the syringe being filled.

The syringe engagement port may comprise one-way valve(s) to restrain mixing of fluids prior to their entry into the syringe undergoing filling. Other structural components may additionally, or alternatively, be used to effect such segregation of different fluids and minimization of mixing upstream of the syringe. For example, the manifold at its axially elongate leg or main flow passage member portion may be partitioned to provide constituent flow passages for each of the respective fluids being delivered to the syringe coupled to the syringe engagement port.

As a specific example of one arrangement of the feed manifold, the syringe engagement port may comprise a distal discharge passage that is coaxial in structure, with an outer annular passage coupled in flow communication to a first fluid carpule, and an inner cylindrical passage coupled in flow communication to a second fluid carpule, so that mixing of the first and second fluids is minimized upstream of the barrel of the syringe undergoing the filling operation.

The respective ones of the multiple carpules in the syringe fill device can be of any suitable size and volume, in relation to one another. For example, the syringe fill device may accommodate multiple carpules of the same size, or carpules that differ in size from one another, to achieve desired ratios of component fluids in the final mixed composition in the filled syringe.

Each carpule may comprise a stopper at a proximal end portion of a carpule housing. The stopper is responsive to axial force on a proximal face thereof so that the stopper in response to the axial force slides forwardly toward a distal end of the housing. The carpule housing in such arrangement is in fluid flow communication with a distal discharge portion of the carpule so that axially forward movement of the stopper causes fluid in the carpule to be discharged from the distal discharge portion. The distal discharge portion may be configured in any suitable manner for engagement with a proximal end portion of a passage member of the feed manifold, e.g., a proximal end portion of a divergent leg of the manifold.

The distal discharge portion of the carpule may be configured to be lockingly engageable with a proximal end portion of the divergent leg or other inlet structure of the feed manifold. Such engagement structure may be adapted for bayonet-type engagement, threadable engagement, snap-fit engagement, or engagement in other manner.

The drive assembly of the syringe fill device in a specific embodiment comprises a motor drive assembly, in which a separate motor is coupled with a drive piston, for each fluid carpule mountable in the interior volume. In this arrangement, each separate motor and its coupled drive piston can be independently actuatable when the motor is powered, so that the drive piston is compressively engaged with a stopper of a corresponding carpule to cause fluid from the carpule to flow through a passageway of the feed manifold to the syringe engagement port thereof. The drive assembly may for example comprise a separate stepper motor for each of the carpules. In other embodiments, the drive assembly can be configured with suitable gearing and mechanical couplings for driving respective pistons from a single drive motor. It will be recognized that the drive assembly can be configured in any of various suitable forms, to effect dispensing of fluid from respective fluid carpules in the syringe fill device.

Thus, the syringe fill device may be configured in a specific embodiment, as comprising a feed manifold mountable in the interior volume, with such feed manifold including (i) passageways with inlets that are adapted to engage fluid carpules when mounted in the interior volume in flow communication with the inlets, and (ii) a syringe engagement port communicating with the passageways, and configured to mate with a distal end of a syringe body so that fluid flowing through the feed manifold flows into the syringe body. The device further includes a drive assembly adapted to be coupled with fluid carpules mountable in the interior volume, and arranged to effect fluid flow from at least one of the fluid carpules through the feed manifold to the syringe engagement port. The housing in this embodiment is configured to receive the distal portion of a syringe body in the interior volume, so that the distal end of the syringe body mates with the syringe engagement port of the feed manifold for filling the syringe with fluid from one or more carpules mounted in the interior volume of the fill station housing.

The syringe fill device may further comprise components or assemblies for maintaining the syringe engagement port and surrounding structure of the syringe fill device sterile in character. For example, the syringe fill device may include a UV lamp that is constructed and arranged to impinge UV radiation on the syringe engagement port and surrounding structure of the syringe fill device, to maintain such sterile conditions. Other sterility-maintaining arrangements may be employed, including fabrication of the syringe engagement port and surrounding structure from an antimicrobial material, e.g., a polymeric material construction containing silver nanoparticles.

In an illustrative embodiment, the drive assembly may comprise a stepper motor drive assembly including a separate stepper motor coupled with a drive piston, for each fluid carpule mountable in the interior volume, with each separate stepper motor and coupled drive piston being independently actuatable when the stepper motor is powered, to enable the drive piston to be compressively engaged with a corresponding carpule to cause fluid from the carpule to flow through a passageway of the feed manifold to the syringe engagement port.

The feed manifold in such illustrative embodiment may be Y-shaped or wishbone-shaped, with an axially elongate leg, and angularly divergent legs. Each of the angularly divergent legs has a proximal end portion adapted for coupling with a distal end portion of a separate fluid carpule, and each of such legs encloses a divergent leg fluid flow passage. Each of the angularly divergent legs has a distal end portion coupled to the axially elongate leg. The axially elongate leg encloses two separate flow passages extending along the axially elongate leg. Each separate flow passage is coupled to a respective one of the divergent leg fluid flow passages. By this arrangement, flows of fluids from separate carpules coupled to the feed manifold are not intermixed with one another in the axially elongate leg. The syringe engagement port and/or the feed manifold in this embodiment may comprise one-way valves to restrict mixing upstream of the syringe being filled.

In order to provide separate fluid flow passages in the axially elongate leg of the feed manifold, the axially elongate leg may be fabricated with a septum element dividing the lumen of the axially elongate leg into separate flow passages. Alternatively, the axially elongate leg may comprise separate bore openings in such leg for the respective fluids, or such separate flow passages may be provided in other arrangements and structural configurations.

The disclosure correspondingly contemplates a syringe fill assembly comprising a syringe fill device of the present disclosure, as variously described above, and a syringe coupled at a distal end thereof to the syringe engagement port of the feed manifold, to enable filling of the syringe with fluid.

Syringes usefully employed with the syringe fill device of the present disclosure can be of any appropriate type and volumetric capacity. For example, such syringes may have a fluid volume that is in a range of from 2 to 20 mL or more. The syringes in some specific embodiments may have a fluid fill volume of 5 mL. In other specific embodiments, the syringes may have a fluid fill volume of 10 mL. The syringes may be of any suitable type for the fluid administration usage for which the syringes are intended.

Syringes employed with the syringe fill device of the present disclosure, in specific embodiments thereof, may be adapted to provide sensory feedback to an operator of the syringe indicative of delivery of a predetermined volume of the composition from the syringe. For example, the syringe may comprise a housing adapted to hold the therapeutic composition for injection delivery to a subject, and a plunger adapted to be slidably translated in the housing to dispense the therapeutic composition for the injection delivery. The housing and plunger in such syringes may be configured with co-acting feedback members that interact with one another during slidable translation of the plunger in the housing, to produce audible and/or kinesiological feedback to the operator of the syringe.

In one embodiment, such co-acting feedback members comprise a detent structure including a protrusion element on one of the housing and plunger, and a concave recipient structure on the other of the housing and structure, which upon engagement with one another during slidable translation of the plunger produce audible and kinesiological feedback to the operator of the syringe.

The disclosure in another aspect relates to a therapeutic composition supply kit, comprising a syringe fill device according to the present disclosure, as variously described herein, and at least one of components (A) and (B):
(A) syringes adapted to be coupled with the syringe fill device for filling thereof; and
(B) carpules of the therapeutic composition or components thereof, adapted for installation in the syringe fill device and coupling with the feed manifold and the drive assembly.

In various embodiments, the therapeutic composition supply kit comprises components (A). In other embodiments, the therapeutic composition supply kit comprises components (B). In still other embodiments, the therapeutic composition supply kit comprises both components (A) and components (B). Other components may likewise be provided in the therapeutic composition supply kit, such as printed instructions including directions for specific syringe fill operations and/or compositions, replacement UV light bulbs for UV sterilization of the syringe engagement port and surrounding structure, batteries or other power supplies or power equipment for the syringe fill device, and any other components that may accessorize or enhance the character and operation of the syringe fill kit comprising same.

It will be appreciated from the foregoing that the syringe fill device and corresponding assemblies and kits of the present disclosure can be variously fabricated and deployed in use to provide a quick and effective fill of syringes with fluid media. The syringe fill device may be provided with a housing having an opening into which the distal end of a syringe is inserted, for locking engagement with the syringe engagement port of the feed manifold disposed in the housing. The engagement may be effected in any suitable manner, as appropriate to provide a fluid-tight coupling of the feed manifold and the syringe being filled.

Figure 24:
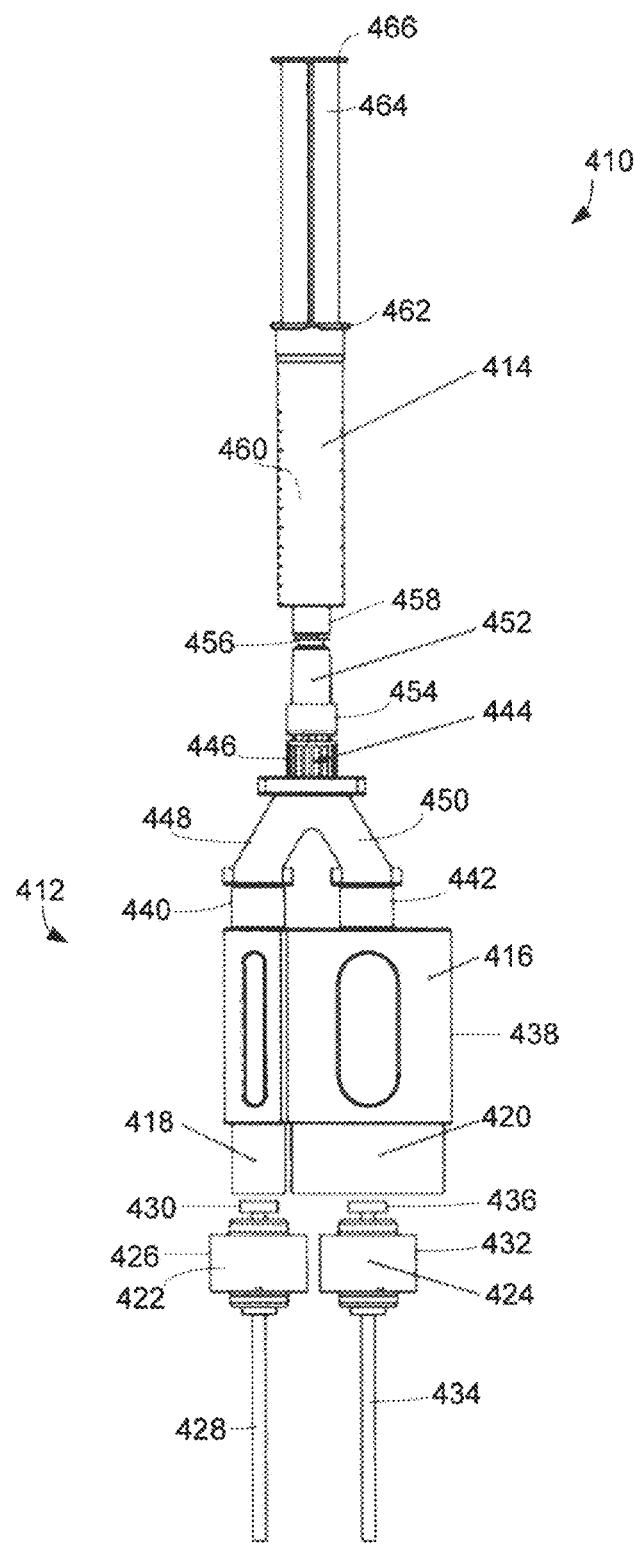
FIG. 24 is a front elevation schematic view of a syringe fill assembly including a syringe fill device in accordance with another embodiment of the present disclosure, as coupled with a syringe for filling.

Referring again to the drawings, FIG. 24 is a front elevation schematic view of a syringe fill assembly including a syringe fill device 412 according to one embodiment of the present disclosure, coupled with a syringe 410 for filling thereof.

The syringe fill device 412 comprises a carpule tray 416 including housing 438 within which are disposed a carpule 418, containing a first fluid, and carpule 420, containing a second fluid.

The housing 438 includes outlets 440 and 442 for the carpules 418 and 420, respectively. The outlets 440 and 442 are configured for coupling with the feed manifold 444, which in the view shown has an inverted Y-shape, comprising angular legs 448 and 450, adapted for coupling with the outlets 440 and 442, respectively. The angular legs 448 and 450 contain internal flow passages 468 and 478, respectively (see FIG. 26) for flowing fluid from the carpules through the feed manifold angular legs to the axially elongate leg 446.

The axially elongate leg 446 encloses a flow passage assembly 492 (see FIG. 26) comprising two separate flow passages, and includes a syringe engagement port 452 threaded by threading 456 at a distal discharge passage 490 thereof (see again FIG. 26) for engagement with syringe 410. The syringe engagement port 452 is coupled to a lower portion of the axially elongate leg by the coupling 454. A source 415 of UV radiation 417 is arranged to irradiate a locus including the syringe engagement port 252, to maintain sterile conditions in the syringe fill operation.

The syringe 410 coupled to the syringe fill device 412 includes a distal end portion 458 extending from a barrel 414 of the syringe. The barrel includes an interior volume 460 in which is disposed a plunger 464. The plunger has a stopper element at a distal face thereof, and a proximal flange 466 that is in abutting relationship with syringe barrel flange 462 when the plunger is fully forwardly advanced to the distal end of syringe 410.

The syringe fill device 412 includes a drive assembly comprising stepper motors 422 and 424. Stepper motor 422 includes motor 426 and axially reciprocable shaft 428 having piston 430 mounted at its distal end. Stepper motor 424 is similarly constructed, as including motor 432 and axially reciprocable shaft 434 with piston 436 mounted at its distal end. The stepper motors in such manner are arranged so that the pistons 430 and 436 can be advanced to apply force to stoppers in the carpules 418 and 420, respectively, to thereby cause fluid to flow from the carpules into the feed manifold 444 for flow to the syringe 410.

Figure 25:
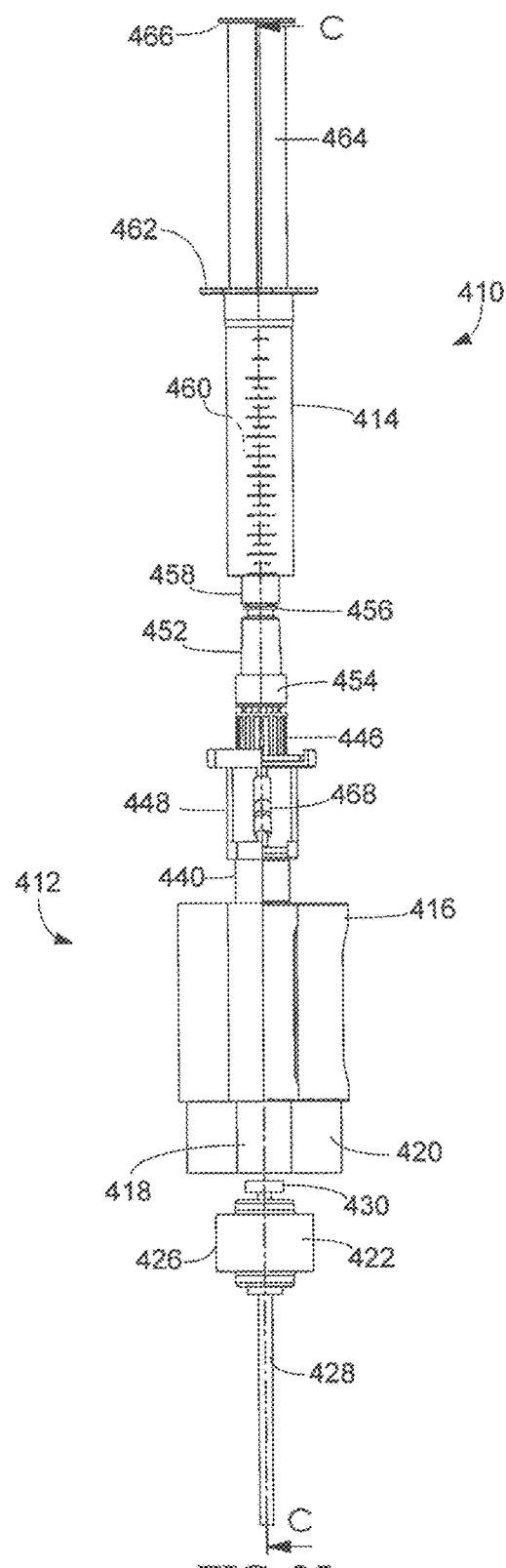
FIG. 25 is a side elevation view of the syringe fill assembly of FIG. 24.

FIG. 25 is a side elevation view of the syringe fill assembly of FIG. 24, wherein corresponding parts are correspondingly numbered for ease of reference.

Figure 26:
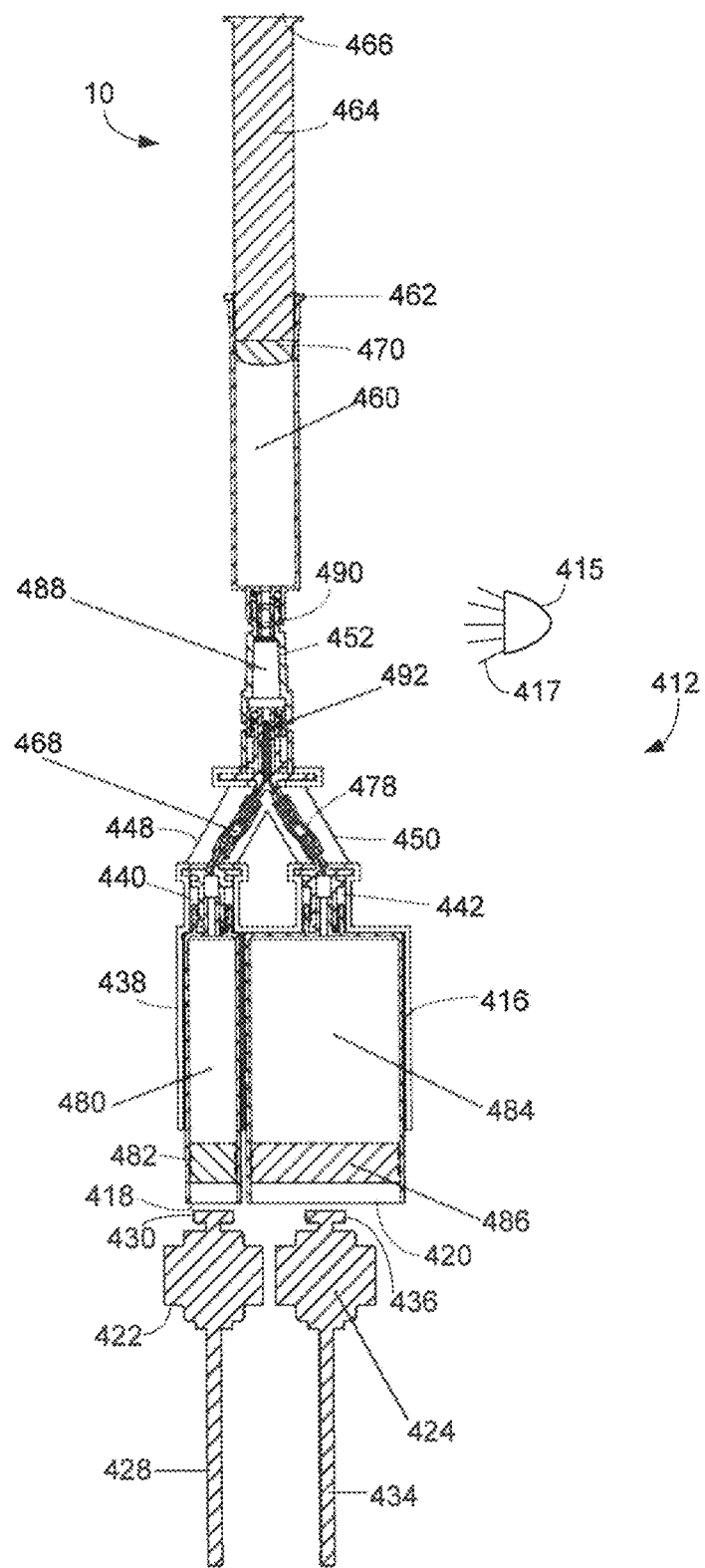
FIG. 26 is a cross-sectional front elevation view of FIGS. 24 and 25, showing the details of construction of the assembly.

FIG. 26 is a cross-sectional front elevation view of FIGS. 24 and 25, showing the details of construction of the assembly. Parts and elements in FIG. 26 are correspondingly numbered with respect to the same parts and elements in FIGS. 24 and 25. As shown, the syringe 410 includes a plunger 464 having a stopper 470 at a distal end thereof. The syringe engagement port 452 is shown as enclosing mixing volume 488. The mixing volume 488 is arranged for receiving fluids from the flow passage assembly 492. The flow passage assembly 492 comprises separate flow passages for each of the fluids from carpules 418 and 420, so that such fluids flow through the discharge volume 488 and distal discharge passage 490 to the interior volume 460 of syringe 410.

The carpules 418 and 420 are shown in FIG. 26 as being equipped with stoppers 482 and 486, respectively, in carpule interior volumes 480 and 484, respectively. The stoppers thereby enclose the fluid volumes in the interior volume of the carpules, and provide a surface against which the pistons 430 and 436 of the drive assembly are abuttingly engaged, so that the stoppers can be forwardly (upwardly in the view shown) advanced, to mediate fluid flow from the carpules to the feed manifold.

Figure 27:
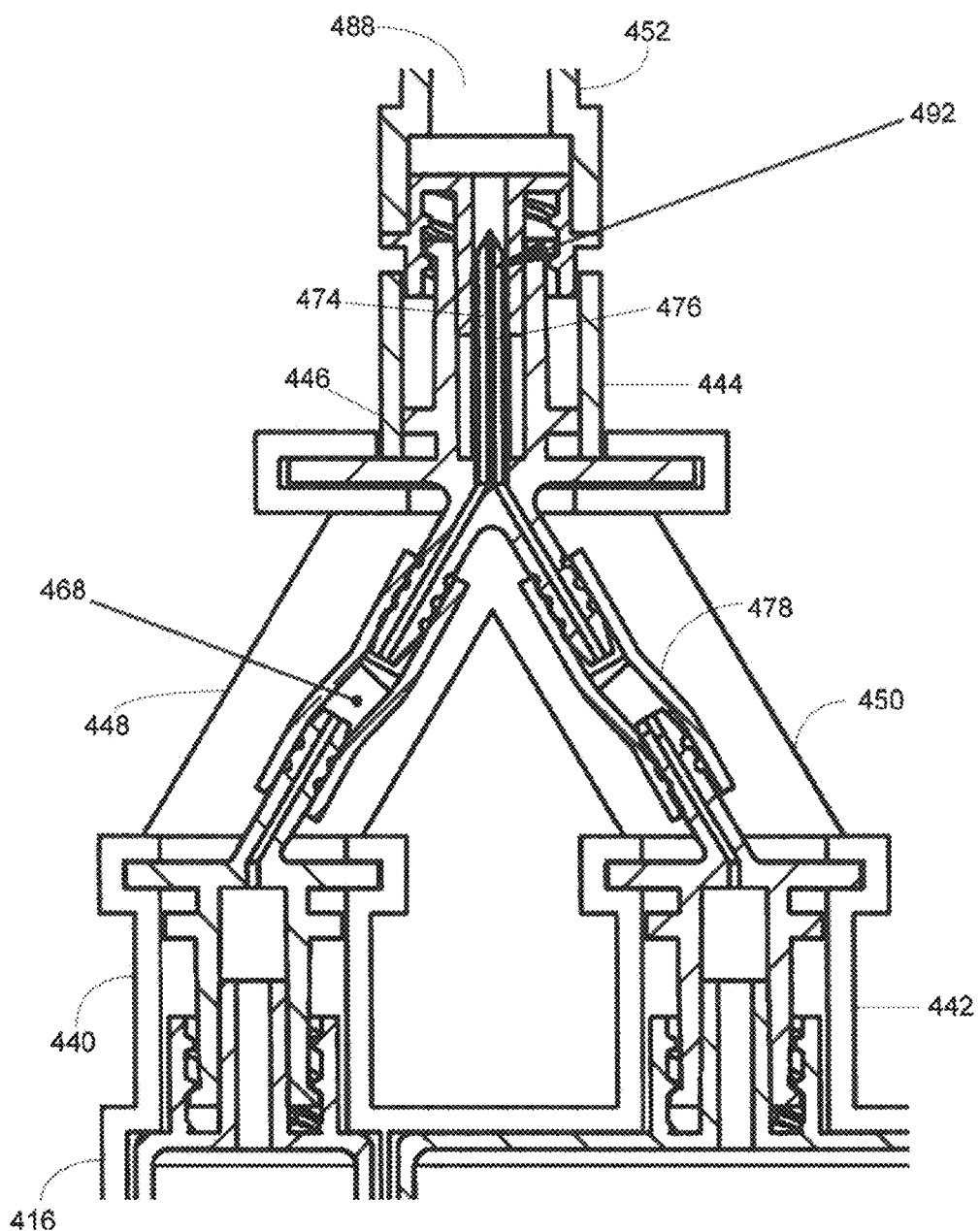
FIG. 27 is an enlarged sectional elevation view of a portion of the feed manifold in the syringe fill device of FIGS. 24-26, showing the details of construction thereof.

FIG. 27 is an enlarged sectional elevation view of a portion of the feed manifold 444 in the syringe fill device of FIGS. 24-26, showing the details of construction thereof. All corresponding parts and elements are numbered in FIG. 27 in correspondence to the numbering of the same parts and elements in FIGS. 24-26.

As illustrated in FIG. 27, the carpule tray 416 includes outlets 440 and 442, to which are coupled the angularly diverging legs 448 and 450 of the feed manifold 444, respectively. Angularly diverging leg 448 contains flow passage 468 therein, and angularly diverging leg 450 contains flow passage 478 therein. These flow passages communicate with separate needle passages 474 and 476 in the flow passage assembly 492 in the axially elongate leg 446 of the feed manifold 444.

By this arrangement, the flows of fluids from separate carpules coupled to the feed manifold are not intermixed with one another in the axially elongate leg, but instead enter the syringe engagement port 452 where the fluids flow through the discharge volume 488 communicating with the axially elongate leg. In this manner, the discharge volume receives the flows of fluids from the separate carpules coupled to the feed manifold, as conveyed from the separate flow passages 474 and 476 extending along the axially elongate leg. Thus, the fluids from the separate carpules flow through the discharge volume 488 of the one-way valve of the feed manifold 444, before flow into the syringe body of the syringe coupled with the feed manifold.

This arrangement provides point-of-use mixing of the fluids from the respective carpules in the syringe barrel interior volume.

Figure 28:
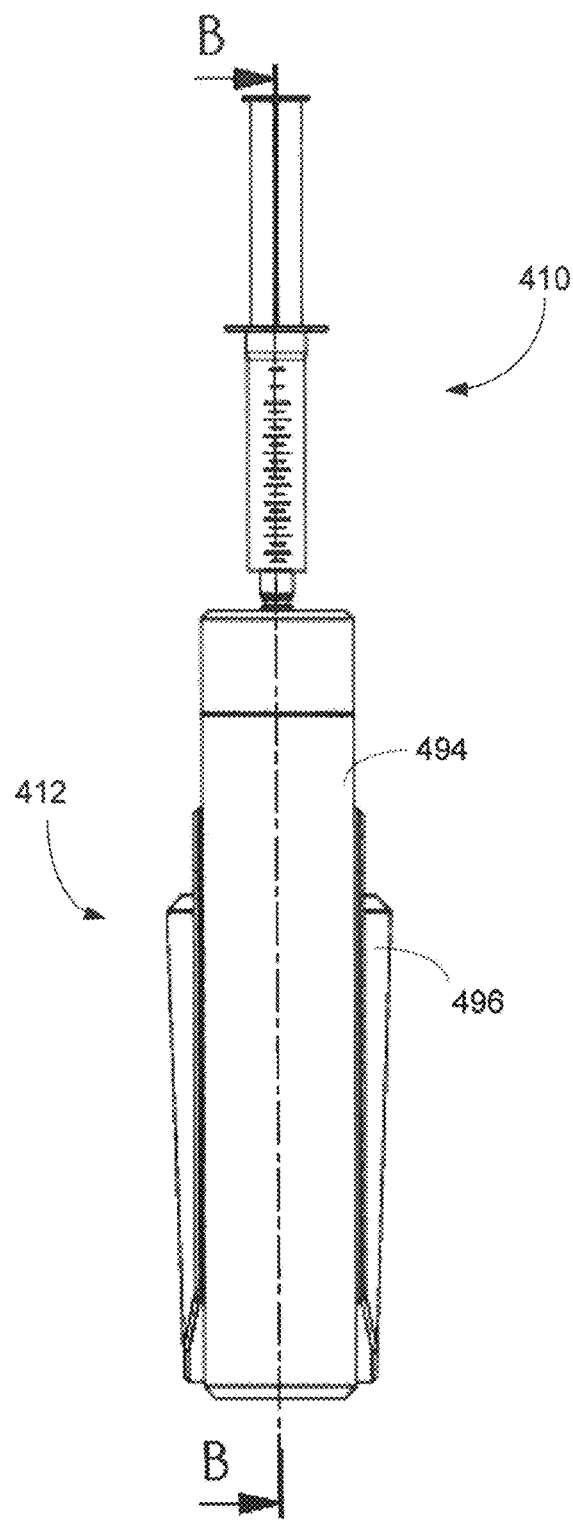
FIG. 28 is a top plan view of the syringe fill assembly of FIGS. 24-27.

FIG. 28 is a top plan view of the syringe fill assembly of FIGS. 24-27, comprising syringe 410 and syringe fill device 412. The syringe fill device 412 advantageously comprises a housing 494 within which are disposed the carpules tray, drive assembly and feed manifold, as previously described. The housing 494 in the construction shown is reposed on base 496.

Figure 29:
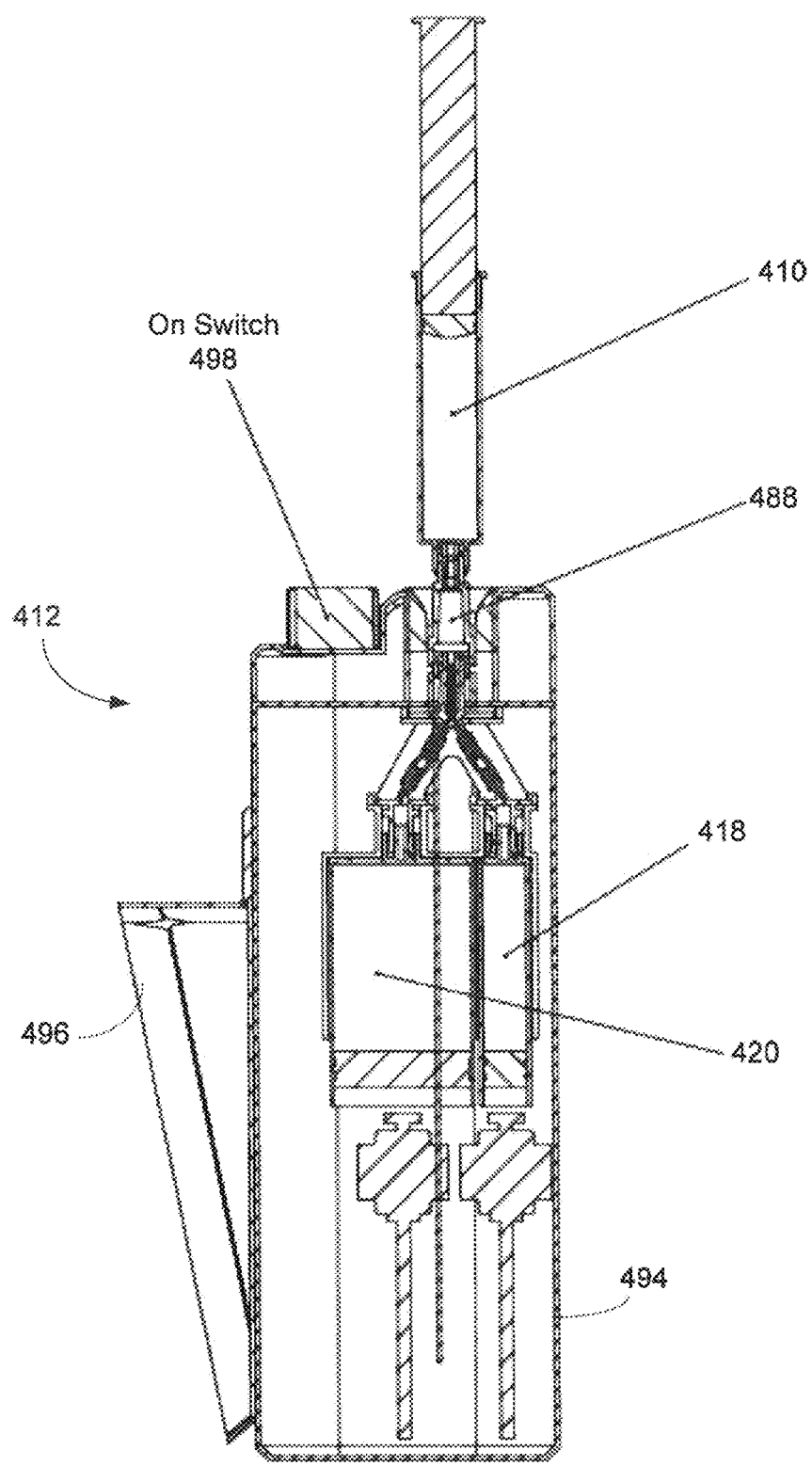
FIG. 29 is a side elevational view, in cross-section, taken along line B-B of FIG. 28

FIG. 29 is a side elevational view, in cross-section, taken along line B-B of FIG. 28, showing the details of the syringe fill assembly comprising syringe 410 and syringe fill device 412. The syringe fill device 412 comprises housing 494 reposed on base 496. The carpules 418 and 420 are shown as mounted in the interior volume of the housing, along with the drive assembly and the feed manifold, including discharge volume 488.

As shown schematically in FIG. 29, the syringe fill device 412 includes on the housing a manually actuatable "On Switch" 498. This switch is coupled to suitable electronic circuitry (not shown) for actuating the stepper motors of the drive assembly to effect the dispensing of fluid from the carpules 418 and 424. By such dispensing action, fluids flow through the passages of the inverted Y-shaped feed manifold to the discharge volume 488 and into the interior volume in the barrel of the syringe 410 for subsequent administration to a patient. Accordingly, manual depression of the switch 498 initiates the fill sequence for the syringe 410.

In various embodiments, additional monitoring and control features may be provided on and/or in the syringe fill device. For example, the syringe fill device may comprise indicator lights, such as LED elements of differing colors, to indicate an operational state or condition of the syringe fill device. In one embodiment, LED elements include a red LED element that when energized indicates that the syringe fill device is not ready for syringe fill operation, and a green LED element that when energized indicates that the syringe fill device is ready for syringe fill operation. The syringe fill device may in various implementations comprise gauges, indicator lights, and/or other output features to provide a user with relevant information for the syringe fill process, such as, without limitation, temperature of fluid in the carpule(s), degree of completion of the fill operation, cumulative number of syringe fill operations performed in a specified time period, volume of the syringe being filled, etc. The syringe fill device may also be provided with data communication and/or signal processing capability, e.g., a port for connection to a data communication or processing network, wireless connectivity to a fluid inventory monitoring system, etc. the syringe fill device may also be equipped with various input features and capability, e.g., settings mechanisms to accommodate a specific sized syringe, type of fluid, etc.

The syringe fill device additionally may be constructed with safety features, e.g., a "lock-out" feature such that the fill sequence is not able to be initiated unless a syringe 410 is fully coupled with the syringe engagement port of the feed manifold, to prevent initiation of fluid dispensing without a syringe mounted to receive the dispensed fluid.

The syringe fill device may also be constructed to incorporate in the interior volume of the housing a heat source such as an electrical resistance heating element or other heater component, serving to maintain the fluids in the respective carpules at temperature appropriate for physiological administration of the fluids. For example, the housing may contain a heater arranged to maintain such fluids at body temperature, to further enhance the administration of the composition comprising the fluid components.

It will be appreciated that the syringe fill device can further be provided with various monitoring and control elements and assemblies, to facilitate the syringe fill operation. For example, the syringe fill device may be arranged to fill 10 mL syringes, and the device may be equipped with visual and/or auditory output capability, to signal an operator when a syringe has been fully filled with 10 mL of therapeutic composition, thereby improving the speed and efficiency of the use of the syringe fill device.

The syringe fill device of the present disclosure may be provided as a constituent of a kit including an array of syringes and/or carpules, together with printed instructions for use of the device in filling syringes with fluids from carpules, and other components, as hereinabove described.

While the disclosure has been described herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A syringe fill system, comprising:
   a housing in which is mounted a pusher arranged to exert downward pressure on a first fluid supply package that is pressure-responsive to dispense fluid, the pusher being coupled with a track in the housing for bidirectional linear movement;
   a selector and driver assembly operatively coupled with the pusher, arranged for user selection of an amount of a first fluid to be dispensed and responsive to the user selection to translate the pusher against the first fluid supply package for dispensing of the user-selected amount of the first fluid; and
   a cassette assembly removably installable in the housing, and comprising a manifold adapted to receive fluid from the first fluid supply package, and configured for coupling with a second fluid supply package, and mixing of the first and second fluids to form a fluid mixture for syringe fill, the manifold including a syringe coupling engageable with a syringe coupling port in the housing, so as to allow a syringe to be coupled with the syringe coupling of the cassette assembly for the syringe fill,
   wherein the syringe fill system is configured for push-pull dispensing of the first and second fluids, respectively, with push dispensing of the first fluid being effected by translation of the pusher against the first fluid supply package to dispense the user-selected amount of the first fluid to a flow passage in the manifold communicating with the syringe coupling port, and with pull dispensing of the second fluid being effected by retraction of a plunger in a barrel of a syringe coupled with the syringe coupling of the cassette assembly, to thereby cause suction to draw second fluid from the second fluid supply package into the flow passage in the manifold for said mixing of the first and second fluids to form the fluid mixture, with purging of the first fluid from the flow passage during syringe fill by retractive action of the plunger so that the fluid mixture is drawn from the flow passage into the syringe during the syringe fill.

2. The syringe fill system of claim 1, wherein the syringe coupling is configured with locking structure for locking the syringe in position for the syringe fill.

3. The syringe fill system of claim 1, wherein the syringe coupling is constructed and arranged for maintaining sterile conditions of a syringe coupled therewith.

4. The syringe fill system of claim 3, wherein the syringe coupling comprises a lockout feature for maintaining sterility of the syringe coupling when a syringe is not coupled to the syringe coupling of the cassette assembly for the syringe fill.

5. The syringe fill system of claim 1, comprising the first fluid supply package and the second fluid supply package disposed in the housing and arranged for fluid mixing in the manifold of the cassette assembly.

6. The syringe fill system of claim 5, wherein the first fluid supply package contains buffering medium, and the second fluid supply package contains an anesthetic for which the buffering medium is bufferingly effective.

7. The syringe fill system of claim 6, wherein the anesthetic comprises an aesthetic selected from the group consisting of lidocaine, articaine, and marcaine.

8. The syringe fill system of claim 1, further comprising check valves configured for the push-pull dispensing of the first and second fluids, respectively, the check valves comprising a first check valve arranged to control push dispensing of the first fluid, and a second check valve arranged to control pull dispensing of the second fluid, the first check valve having a crack pressure in a range of from 6 to 20 psi, and the second check valve having a crack pressure in a range of from 0.5 to 10 psi, with the proviso that the crack pressure of the first check valve is higher than the crack pressure of the second check valve.

9. The syringe fill system of claim 8, wherein the first fluid comprises buffering medium, and the second fluid comprises an anesthetic for which the buffering medium is bufferingly effective.

10. The syringe fill system of claim 9, wherein the anesthetic comprises an aesthetic selected from the group consisting of lidocaine, articaine, and marcaine.

11. A syringe fill system, comprising:
    a housing in which is mounted a pusher arranged for push dispensing of fluid from a first fluid supply package;
    a selector and driver assembly operatively coupled with the pusher, for push dispensing of a user-selected amount of the first fluid; and
    a cassette assembly removably installable in the housing, and comprising a manifold adapted to receive fluid from the first fluid supply package, and configured for coupling with a second fluid supply package, and mixing of the first and second fluids to form a fluid mixture for syringe fill, the manifold including a syringe coupling for engaging a syringe and filling the syringe with the fluid mixture,
    wherein the syringe fill system is configured for push-pull dispensing of the first and second fluids, respectively, with push dispensing of the first fluid being effected by translation of the pusher against the first fluid supply package to dispense the user-selected amount of the first fluid to a flow passage in the manifold communicating with the syringe coupling, and with pull dispensing of the second fluid being effected by retraction of a plunger in a barrel of a syringe coupled with the syringe coupling, to thereby cause suction to draw second fluid from the second fluid supply package into the flow passage in the manifold for said mixing of the first and second fluids to form the fluid mixture, with purging of the first fluid from the flow passage during syringe fill by retractive action of the plunger so that the fluid mixture is drawn from the flow passage into the syringe during the syringe fill.

12. The syringe fill system of claim 11, wherein the syringe coupling is configured with locking structure for locking the syringe in position for syringe filling.

13. The syringe fill system of claim 11, wherein the syringe coupling is constructed and arranged for maintaining sterile conditions of the syringe engaged therewith.

14. The syringe fill system of claim 13, wherein the syringe coupling comprises a lockout feature for maintaining sterility of the syringe coupling when a syringe is not engaged with the syringe coupling of the cassette assembly for syringe filling.

15. The syringe fill system of claim 11, comprising the first fluid supply package and the second fluid supply package disposed in the housing and arranged for fluid mixing in the manifold of the cassette assembly.

16. The syringe fill system of claim 15, wherein the first fluid supply package contains buffering medium, and the second fluid supply package contains an anesthetic for which the buffering medium is bufferingly effective.

17. The syringe fill system of claim 16, wherein the anesthetic comprises an aesthetic selected from the group consisting of lidocaine, articaine, and marcaine.

18. The syringe fill system of claim 11, further comprising check valves configured for the push-pull dispensing of the first and second fluids, respectively, the check valves comprising a first check valve arranged to control push dispensing of the first fluid, and a second check valve arranged to control pull dispensing of the second fluid, the first check valve having a crack pressure in a range of from 6 to 20 psi, and the second check valve having a crack pressure in a range of from 0.5 to 10 psi, with the proviso that the crack pressure of the first check valve is higher than the crack pressure of the second check valve.

19. The syringe fill system of claim 18, wherein the first fluid comprises buffering medium, and the second fluid comprises an anesthetic for which the buffering medium is bufferingly effective.

20. The syringe fill system of claim 19, wherein the anesthetic comprises an aesthetic selected from the group consisting of lidocaine, articaine, and marcaine.

* * * * *

UNITED STATES PATENT AND TRADEMARK OFFICE
CERTIFICATE OF CORRECTION

PATENT NO. : 10,010,482 B2  
APPLICATION NO. : 15/208568  
DATED : July 3, 2018  
INVENTOR(S) : Daniel K. Davidian Page 1 of 1

It is certified that error appears in the above-identified patent and that said Letters Patent is hereby corrected as shown below:

In the Specification

Column 2, Line 3: "Tillable" should be -- fillable --.

Column 5, Line 50: "Tillable" should be -- fillable --.

Column 13, Line 36: "Lake Forest, Ill." should be -- Lake Forest, IL. --.

Signed and Sealed this  
Twenty-eighth Day of May, 2019

Andrei Iancu  
*Director of the United States Patent and Trademark Office*